Figure 1:
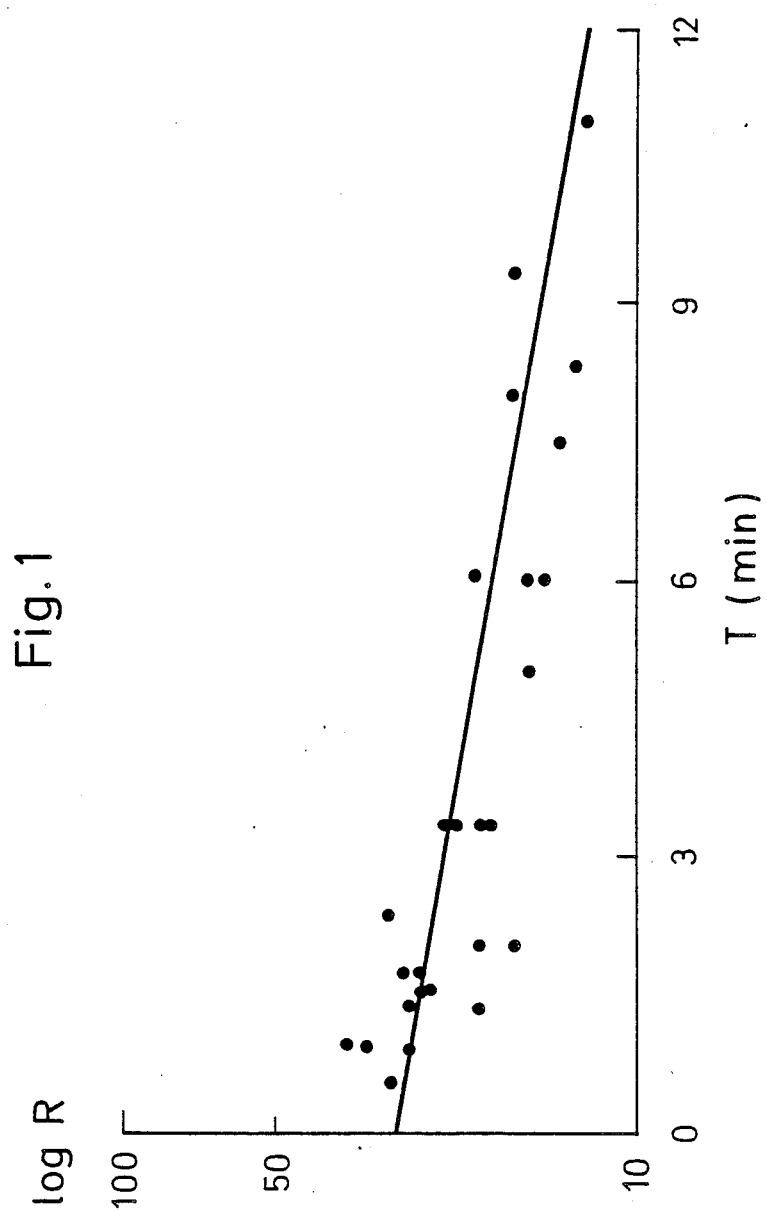

United States Patent [19]

Wulf

[11] Patent Number: 4,882,598

[45] Date of Patent: Nov. 21, 1989

[54] METHOD AND AN APPARATUS FOR DETERMINING AN INDIVIDUAL'S ABILITY TO STAND EXPOSURE TO ULTRAVIOLET RADIATION

[75] Inventor: Hans C. Wulf, Charlottenlund, Denmark

[73] Assignee: Chromo-Light ApS, Charlottenlund, Denmark

[21] Appl. No.: 80,886

[22] PCT Filed: Sep. 26, 1986

[86] PCT No.: PCT/DK86/00108

§ 371 Date: Jul. 24, 1987

§ 102(e) Date: Jul. 24, 1987

[87] PCT Pub. No.: WO87/01948

PCT Pub. Date: Apr. 9, 1987

[30] Foreign Application Priority Data

Sep. 26, 1985 [DK] Denmark ............... 4370/85
Oct. 24, 1985 [DK] Denmark ............... 4894/85

[51] Int. Cl.$^4$ .............................. G01J 1/00; G01J 1/42
[52] U.S. Cl. .................... 250/338.1; 250/372
[58] Field of Search ............ 250/372, 338 R; 364/414

[56] References Cited

U.S. PATENT DOCUMENTS

| | | | |
|---|---|---|---|
| 3,917,948 | 11/1975 | Strutz | 250/372 |
| 4,212,535 | 7/1980 | Sanders et al. | 250/372 |
| 4,226,540 | 10/1980 | Barten et al. | 356/445 |
| 4,428,050 | 1/1984 | Pellegrino et al. | 250/372 |
| 4,704,535 | 11/1987 | Leber et al. | 250/372 |
| 4,749,865 | 6/1988 | Scheller | 250/372 X |

FOREIGN PATENT DOCUMENTS 0046158 2/1982 European Pat. Off. .

Primary Examiner—David Mis
Attorney, Agent, or Firm—Birch, Stewart, Kolasch & Birch

[57] ABSTRACT

In accordance with a method and an apparatus for determining an individual's ability to stand exposure to ultraviolet radiation prior to causing a skin reaction, such as skin cancer or erythema, or for determining an individual's ability to become tanned by exposure to ultraviolet radiation, at least part of the individual's skin surface is exposed to electromagnetic radiation of a predetermined spectral composition, e.g. visible light, and of a predetermined intensity. The intensity of electromagnetic radiation reflected from the part of the individual's skin surface is measured so as to determine the coefficient of reflection of the part exposed to electromagnetic radiation of the predetermined spectral composition. The coefficient of reflection is converted into logarithmic representation and the logarithmic representation of the coefficient of reflection constitutes a measure representing the individual's ability to stand exposure to ultraviolet radiation prior to causing said skin reaction, or into a measure representing said individual's ability to become tanned by exposure to ultraviolet radiation.

73 Claims, 15 Drawing Sheets

METHOD AND AN APPARATUS FOR DETERMINING AN INDIVIDUAL'S ABILITY TO STAND EXPOSURE TO ULTRAVIOLET RADIATION

It is a well-known fact that ultraviolet radiation, i.e. electromagnetic radiation within the wavelength range of 100-400 nm, may cause biological skin effects and even severe skin diseases. Thus, exposure to ultraviolet radiation may result in erythema, and excessive exposure to ultraviolet radiation may further result in skin cancer, destruction of elastic skin fibres, generation of D-vitamins, immunological changes, etc.

Ultraviolet radiation is usually divided into four ultraviolet wavelength bands or ranges, a first one of which is the wavelength range of 100-200 nm, a second one of which is the wavelength range of 200-280 nm (conventionally designated UVC), a third one of which is the wavelength range of 280-320 nm (conventionally designated UVB), and a fourth one of which is the wavelength range of 320-400 nm (conventionally designated UVA). The wavelength range of 100-200 nm is of little practical importance since electromagnetic radiation within this wavelength range is absorbed in the air of the atmosphere.

The UVC radiation is absorbed in the stratosphere by the ozone layer and is therefore not present in sunlight in the earth level. However, UVC radiation is produced in connection with welding, sterilization by ultraviolet radiation, artificial ultraviolet ray tubes or bulbs, etc.

It has been realised that UVB radiation is the main skin cancer causing ultraviolet wavelength band or range. UVB radiation is present in sunlight and is also produced by numerous artificial light and ultraviolet light sources. UVA radiation is present in sunlight and in light produced by artificial light and ultraviolet light sources.

It is well-known that individuals with a light skin complexion cannot stand the same extent of exposure to ultraviolet radiation as individuals with a dark skin complexion. The former often produce erythema even after short periods of exposure to ultraviolet radiation and are probably also more susceptible to develop skin cancer after exposure, such as excessive exposure, to ultraviolet radiation.

In spite of the above no reliable measuring method or apparatus has been deviced by means of which an individual's ability to stand exposure to ultraviolet radiation prior to causing a skin reaction, such as skin cancer or erythema, or by means of which an individual's ability to become tanned by exposure to ultraviolet radiation can be determined.

It is therefore an object of the present invention to provide a method rendering it possible to determine an individual's ability to stand exposure to ultraviolet radiation prior to causing a skin reaction, such as skin cancer or erythema, or to determine an individual's ability to become tanned by exposure to ultraviolet radiation and further to provide an apparatus by means of which an individual's ability to stand exposure to ultraviolet radiation prior to causing a skin reaction, such as skin cancer or erythema, or by means of which an individual's ability to become tanned by exposure to ultraviolet radiation can be determined.

A further object of the present invention is to provide a method of controlling an individual's exposure to ultraviolet radiation for tanning said individual's skin surface in order to render it possible to expose said individual's skin surface to ultraviolet radiation without running the risk of becoming erythrodermic or erythematous or catching more serious skin diseases, such as skin cancer.

A still further object of the present invention is to provide an apparatus for dosimetrically measuring an UV-radiation dosis or electromagnetic radiation in general, e.g. visible light, which apparatus renders it possible to provide reproducible and highly accurate measuring results.

In a first aspect of the present invention, a method of determining an individual's ability to stand exposure to ultraviolet radiation prior to causing a skin reaction, such as skin cancer or erythema, or of determining an individual's ability to become tanned by exposure to ultraviolet radiation is provided, said method comprising the following steps:

exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said part to said electromagnetic radiation of said predetermined spectral composition, and converting said coefficient of reflection into a measure representing said individual's ability to stand exposure to ultraviolet radiation prior to causing said skin reaction or into a measure representing said individual's ability to become tanned by exposure to ultraviolet radiation.

Said measure may be of the type expressing that the individual can/cannot stand exposure to further ultraviolet radiation, i.e. of a discontinuous type expressing a specific threshold or be of a continuous measure, such as a scale.

Basically, in accordance with the teaching of the present invention, it has been realised that an individual's ability to stand exposure to ultraviolet radiation prior to causing a skin reaction corresponds to the individual's coefficient of skin surface reflection to electromagnetic radiation. Thus, it has been realised, as will be evident from the detailed description below, that the correspondence between the individual's ability to stand exposure to ultraviolet radiation prior to erythema and the individual's coefficient of skin surface reflection to electromagnetic radiation is of a logarithmic nature.

A number of individuals have been tested in that their coefficients of skin surface reflection to electromagnetic radiation have been determined, and the period of time during which the individuals were to be exposed to ultraviolet radiation of a predetermined spectral composition and of a predetermined intensity in order to just about produce erythema was recorded. A linear dependency between the periods of time of exposure to ultraviolet radiation and the logarithmic representation of the coefficients of skin surface reflection to electromagnetic radiation was demonstrated. It is believed that a similar long time and short time exposure relation is valid also in connection with other skin reactions, such as skin cancer which is believed to have its origin, as far as the ultraviolet radiation exposure reaction is concerned, in the following reaction sequence: inflammation, vasodilation, epithelial injury, immunological variation, and cancer.

Consequently, said step of converting said coefficient of reflection into a measure may, in accordance with the preferred embodiment of the method according to the invention, comprise:

converting said coefficient of reflection into logarithmic representation.

The electromagnetic radiation to which the individual's skin surface is exposed in order to determine the individual's coefficient of skin surface reflection may preferably comprise spectral components within a wavelength range of 200–800 nm, preferably 400–700 nm, and consequently spectral components of visible light.

The conversion of the individual's coefficient of reflection into a measure representing the individual's ability to stand exposure to ultraviolet radiation prior to causing said skin reaction or into a measure representing said individual's ability to become tanned by exposure to ultraviolet radiation is, as mentioned above, based upon an empirical realisation. It is believed that the method of the present invention may be employed in connection with any ultraviolet radiating sources whether natural or artificial, such as the sun or ultraviolet ray tubes or bulbs, welding apparatuses, sterilisation apparatuses, etc. In some applications, the intensity of the ultraviolet radiating source is known, and the coefficient of reflection may, in accordance with a further embodiment of the method according to the invention, be converted into a measure representing a maximum time of exposure to an ultraviolet radiation source of said spectral composition and of said predetermined intensity, or a maximum permissible time of exposure to ultraviolet radiation or light in a combined medicinal and ultraviolet light (UVA)-treatment, a so-called PUVA-treatment (Psoralen-product, such as 8-methoxypsoralene, and UVA-treatment). Alternatively, the method may, in accordance with a further embodiment, comprise measuring the intensities of electromagnetic radiation within the wavelength ranges of 200–280 nm (UVC), 280–320 nm (UVB), and 320–400 nm (UVA), and the coefficient of reflection of said individual may be converted into a measure representing the individual's ability to stand exposure to electromagnetic radiation of said intensities taking into consideration the erythema action spectrum, the cancer action spectrum, the pigmentation action spectrum or any other action spectrum. The conversion of the coefficient of reflection into said measure preferably results in a representation of the individual's maximum time of exposure to an ultraviolet radiating source of said intensities within the UVC, UVB and UVA bands. The conversion may be performed as a weighting of the intensities within the UVC, UVB and UVA bands taking into consideration the above described different skin effects of the individual ranges, e.g. in accordance with the erythema action spectrum, the cancer action spectrum, the pigmentation action spectra or any other action spectra.

It is to be realised that the individual, whose ability to stand exposure to ultraviolet radiation prior to erythema is to be determined in accordance with the present invention, has to be non-erythrodermic or non-erythematous since an erythrodermic or erythematous individual cannot stand exposure to ultraviolet radiation to any substantial extent. In the sun or in solaria, individuals may wish to sun bathe, although they are erythrodermic or erythematous. In case an already erythrodermic or erythematous individual has his or her coefficient of skin surface reflection to electromagnetic radiation determined in accordance with the method of the present invention, the measure representing the individual's ability to stand exposure to ultraviolet radiation may indicate that the individual may stand the exposure for some time. However, since the individual is already erythrodermic or erythematous, the measure should preferably indicate that the individual cannot stand further exposure to ultraviolet radiation. Consequently, the method according to the invention may further comprise:

determining the coefficients of reflection of said skin surface part to electromagnetic radiation of at least a first and a second wavelength, said first wavelength being a wavelength, at which erythrodermic or erythematous skin reflection is high, and said second wavelength being a wavelength, at which erythrodermic or erythematous skin reflection is low, and comparing said coefficients of reflection so as to determine if said skin surface part is already erythrodermic or erythematous.

In case the individual is not erythrodermic or erythematous, the coefficients of reflection at said first and said second wavelengths will not differ from one another to the same extent as when the individual is erythrodermic or erythematous, whereas the coefficients of reflection at said first and said second wavelengths will be highly different from one another in case the individual is already erythrodermic or erythematous.

Said first wavelength may be of the order of approximately 500–520 nm such as 503–512 nm, and said second wavelength may be of the order of approximately 535–540 nm such as 538 nm or approximately 570–580 nm such as 574–578 nm.

In a second aspect of the present invention, an apparatus for determining an individual's ability to stand exposure to ultraviolet radiation prior to causing a skin reaction, such as skin cancer or erythema, or of determining an individual's ability to become tanned by exposure to ultraviolet radiation is provided, said apparatus comprising:

an electromagnetic source for generating electromagnetic radiation, an electromagnetic detector for detecting the intensity of any electromagnetic radiation exposed to said detector and for generating an electrical signal in response to said exposure to said electromagnetic radiation, a first means for directing at least part of said electromagnetic radiation generated by said electromagnetic source to a part of said individual's skin surface so as to expose said part of said individual's skin surface to electromagnetic radiation of a predetermined spectral composition and of a predetermined intensity, a second means for directing electromagnetic radiation reflected from said part of said individual's skin surface to said electromagnetic detector, and a measuring and converting means connected to said electromagnetic detector for measuring and converting said electrical signal generated by said electromagnetic detector into a measure representing said individual's ability to stand exposure to ultraviolet radiation prior to causing said skin reaction or into a measure representing said individual's ability to become tanned by exposure to ultraviolet radiation.

The apparatus according to the second aspect of the present invention may be implemented in accordance with any of the above embodiments of the method according to the invention.

In accordance with the presently preferred embodiment of the apparatus according to the invention, the apparatus further comprises:

a central control means controlling the overall operation of the apparatus and further controlling the conversion of said electrical signal into said measure.

The central control means may be a microprocessor means and may further include a storage means for storing a schedule representing said conversion of said electrical signal into said measure. As described above, the conversion of said electrical signal generated by said electromagnetic detector and representing the intensity of said electromagnetic radiation reflected from said part of the individual's skin surface and further representing the coefficient of reflection of said skin surface part of the individual is based on empirical results which may be converted into a schedule.

Although the apparatus according to the invention may present the result of the conversion, i.e. said measure, to the individual or to a solarium operator or an operator of a welding apparatus, a sterilisation apparatus, etc., by means of any information means such as a printer, an audio transducer, the apparatus according to the invention preferably comprises a display means connected to said measuring and converting means for displaying said measure to the individual or to the operator. The displaying of the measure may, as mentioned above, be a representation of a maximum permissible period of time of exposure to an ultraviolet radiation source of a predetermined intensity or a source the intensities of which, in the UVC, UVB and UVA bands or ranges, are further determined by means of a third means of the apparatus, and which are weighted as mentioned above taking into consideration the above action spectra.

The apparatus according to the invention may be implemented in a battery-powered, mains supplied, solar cell powered and stationary apparatus or in a portable apparatus which may be powered by batteries or solar cells.

In a third aspect of the present invention, a further method of determining an individual's ability to stand exposure to ultraviolet radiation prior to causing a skin reaction, such as skin cancer or erythema, or of determining an individual's ability to become tanned by exposure to ultraviolet radiation is provided, said method comprising the following steps:

comparing at least part of said individual's skin surface to a skin colour reference scale including a plurality of skin colour reference scale markings so as to determine a skin colour reference scale marking characteristic of said individual on said skin colour reference scale, and converting said individual's skin colour reference scale marking into a measure representing said individual's ability to stand exposure to ultraviolet radiation prior to causing said skin reaction or into a measure representing said individual's ability to become tanned by exposure to ultraviolet radiation.

In accordance with this further or third aspect of the present invention, the individual's ability to stand exposure to ultraviolet radiation or ability to become tanned is determined manually by means of said skin colour reference scale.

The methods according to said first and said third aspects of the present invention are inherently based on one and the same realisation, viz. the empirical realisation of the correspondence between an individual's ability to stand exposure to ultraviolet radiation prior to causing a skin reaction, such as skin cancer or erythema, or of determining an individual's ability to become tanned by exposure to ultraviolet radiation and the individual's coefficient of skin surface reflection to electromagnetic radiation. It is to be realised that the tanning of a skin surface part and the ability of said skin surface part to reflect visible light, e.g. said skin surface part of the individual, express one and the same physical phenomenon. It is further to be realised that a method according to said third aspect of the present invention is preferably employed in connection with non-erythrodermic or non-erythematous individuals, although it is believed that said colour reference scale, to which the individual's skin surface is compared, may further comprise at least one reference scale marking indicating that the individual is erythrodermic or erythematous, and the method according to said third aspect of the present invention may further comprise:

comparing at least said part of said individual's skin surface to said one reference scale marking of the reference scale so as to determine if said individual or at least said part of said individual's skin is erythrodermic or erythematous or not.

In a fourth aspect of the present invention, a skin colour reference scale for carrying out the above method according to said third aspect of the invention is provided, said skin colour reference scale comprising:

a plurality of skin colour reference scale markings to which at least part of said individual's skin surface is to be compared so as to determine a skin colour reference scale marking characteristic of said individual on said skin colour reference scale.

The skin colour reference scale according to the invention may further comprise at least one reference scale marking indicating that the individual is erythrodermic or erythromatous so as to render it possible to determine if the individual is erythrodermic or erythromatous or not.

In a fifth aspect of the present invention, a method of controlling an individual's exposure to ultraviolet radiation is provided, said method comprising the following steps:

determining if said individual's skin surface is easily tanned by exposure to ultraviolet radiation or if said individual's skin surface is not easily tanned by exposure to ultraviolet radiation, and exposing said individual's skin surface to ultraviolet radiation of the wavelength range of 320–400 nm (UVA) exclusively, provided said individual's skin surface has been determined as being easily tanned by exposure to ultraviolet radiation, or alternatively, additionally exposing for a short period of time said individual's skin surface to a low intensity ultraviolet radiation of the wavelength range of 280–320 nm (UVB) or part thereof, provided said individual's skin surface has been determined as not being easily tanned by exposure to ultraviolet radiation so as to start melanogenesis by stimulation of the melanocytes.

In accordance with the above fifth aspect of the present invention, the determination step may be carried out in accordance with the above first aspect of the present invention.

In a sixth aspect of the present invention, an apparatus for dosimetrically measuring an UV-radiation dosis or electromagnetic radiation in general, e.g. visible light, is provided, said apparatus comprising:

an ultraviolet filtering assembly including at least one filter of a specific filtering response for receiving ultraviolet radiation at an input of the ultraviolet filtering assembly and for filtering the ultraviolet radiation output from the ultraviolet filtering assembly in accordance with said specific filtering response of said at least one filter thereof, a light detector for receiving ultraviolet radiation from said filtering assembly and for generating an electric signal in response to said ultraviolet radiation received from said filtering assembly, and an accumulator means for receiving said signal from said light detector and for cumulatively registering said signal, said ultraviolet filtering assembly and said light detector together defining a specific ultraviolet response characteristic.

In the apparatus according to the invention for dosimetrically measuring an UV-radiation dosis, said light detector is preferably a GaPdetector. Furthermore, said accumulator means of the apparatus may, in accordance with a further embodiment of the apparatus, be constituted by a coulometer cell or alternatively be constituted by an electronic measuring means.

The apparatus according to the invention for dosimetrically measuring an UV-radiation dosis may advantageously further comprise a diffusor for receiving and directing said ultraviolet radiation to said input of said ultraviolet filtering assembly, said diffusor having a substantially cosine response.

The filtering assembly of the apparatus according to the invention may further, in accordance with the teachings of the present invention, be of the transmission filtering type, of the reflection filtering type, of the holographic type or of any combination thereof.

In accordance with the teaching of the present invention, the apparatus for dosimetrically measuring an UV-radiation dosis is preferably of a construction in which said specific ultraviolet response characteristic is a UVA response, a UVB response, a UVC response, an erythema action response, a cancer action response, a pigmentation action response or any other response.

Figure 2:
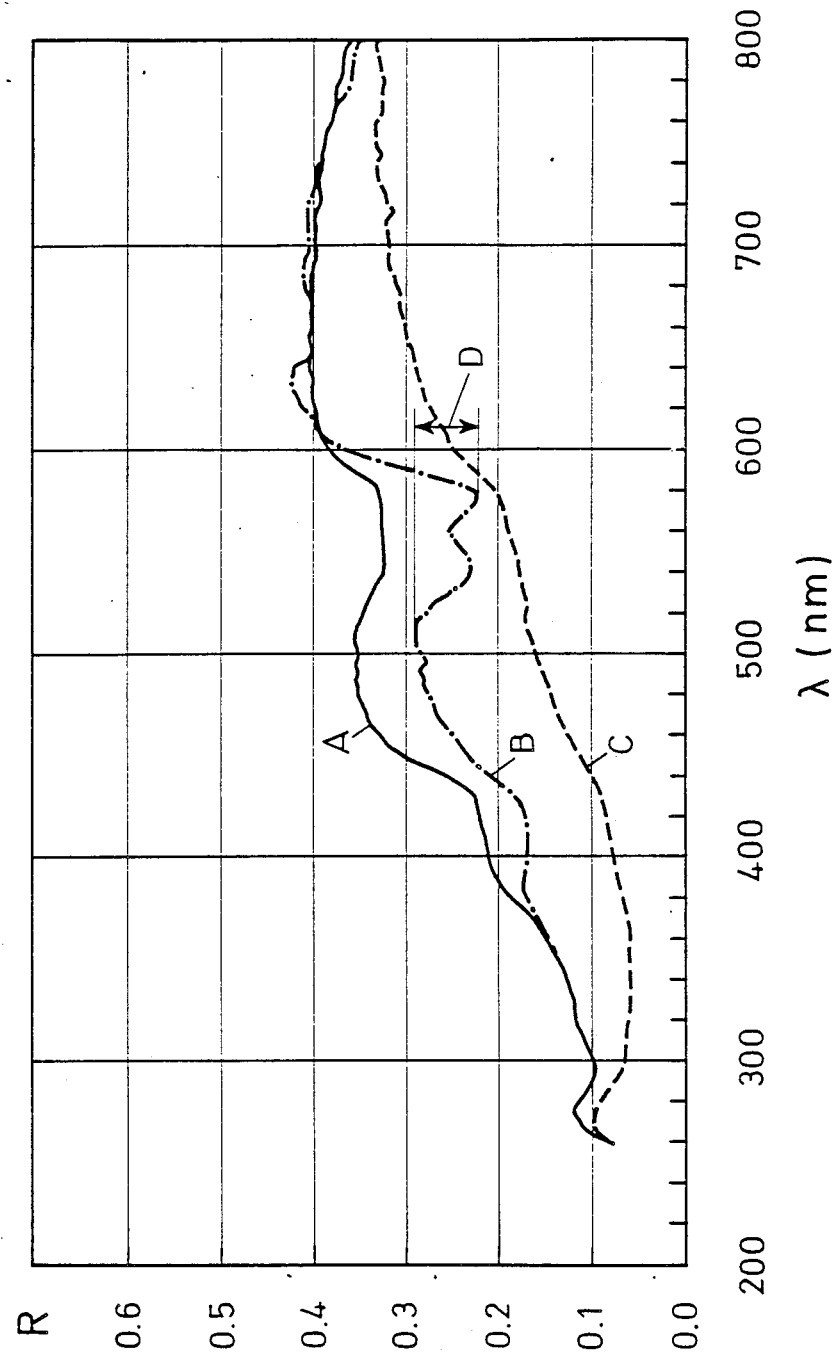
Figure 3:
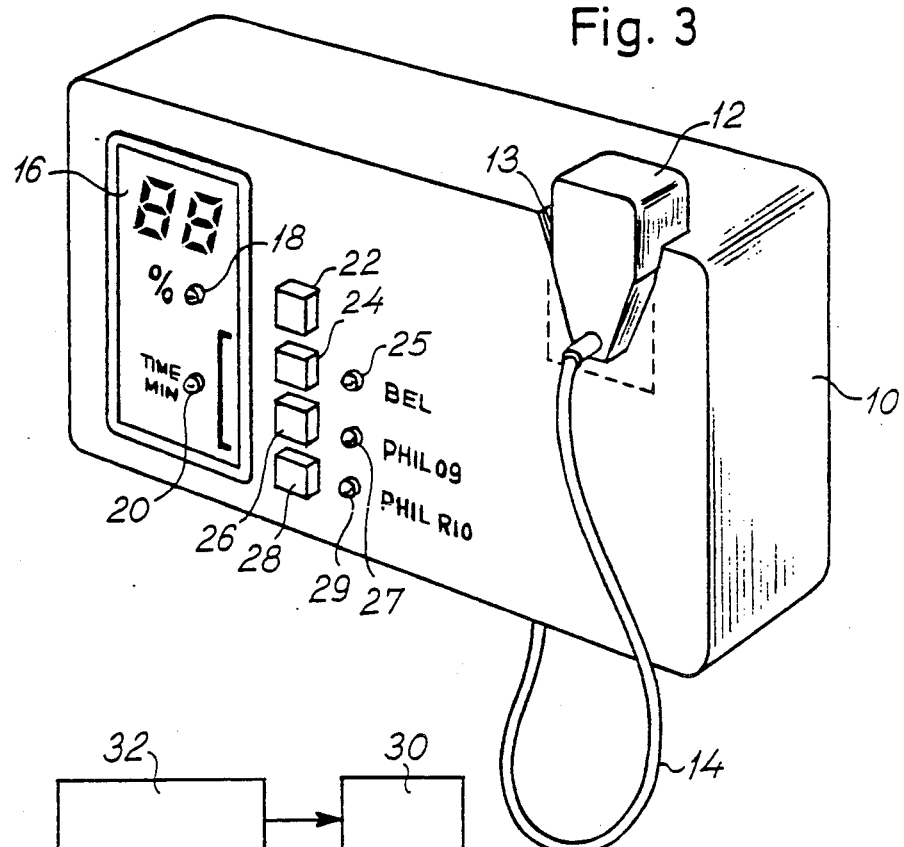
Figure 4:
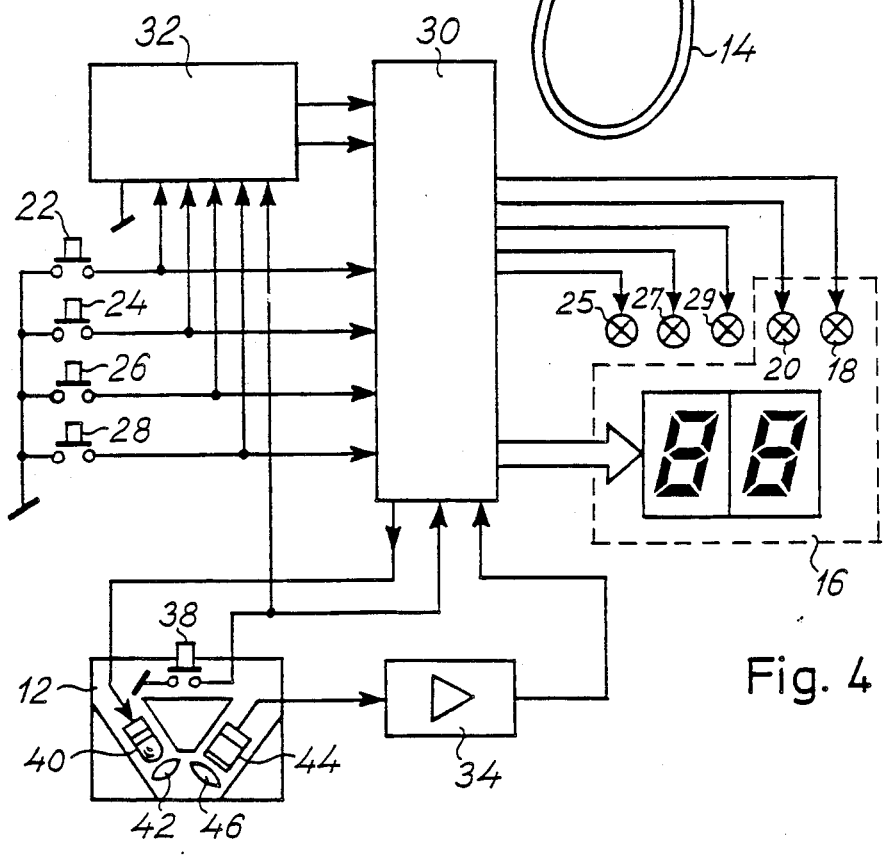
Figure 5:
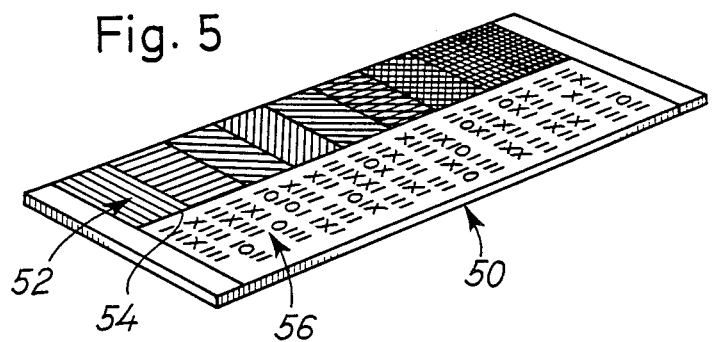
Figure 6:
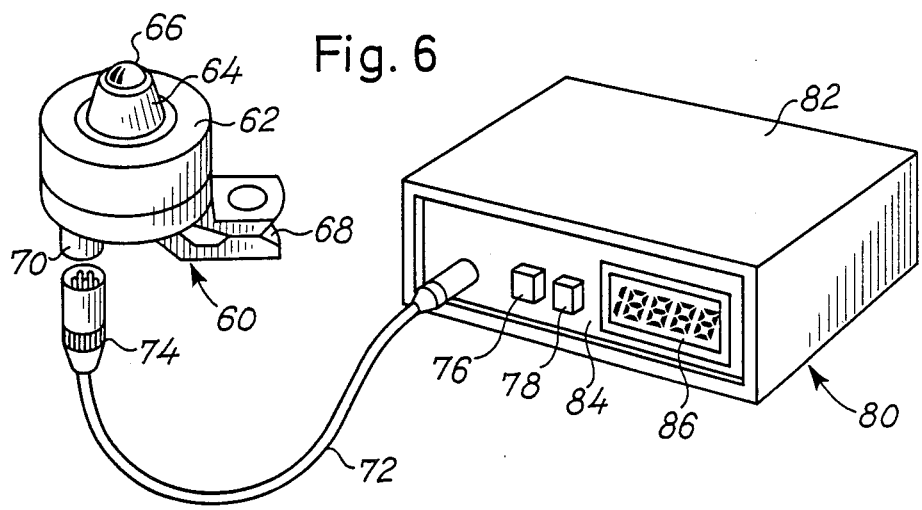
Figure 17:
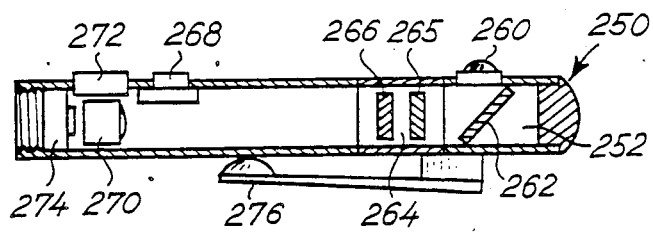

The invention will now be further described with reference to the drawings, wherein FIG. 1 is a diagram illustrating the linear relationship between the logarithmic representation of a number of individuals' coefficients of skin surface reflection and the individuals' ability to stand exposure to ultraviolet radiation of a predetermined intensity and of a predetermined spectral composition, FIG. 2 is a diagram illustrating the coefficients of skin surface reflection of an untanned individual, an erythrodermic individual and a non-erythrodermic and pigmented individual, respectively, as a function of the wavelength of the electromagnetic radiation, FIG. 3 is a perspective and diagrammatical view of a presently preferred embodiment of a stationary implementation of an apparatus for determining an individual's ability to stand exposure to ultraviolet radiation prior to causing a skin reaction, such as skin cancer or erythema, or for determining an individual's ability to become tanned by exposure to ultraviolet radiation according to the invention, FIG. 4 is a block diagram of the electronic circuit of the presently preferred embodiment of the apparatus for determining an individual's ability to stand exposure to ultraviolet radiation prior to causing a skin reaction, such as skin cancer or erythema, or for determining an individual's ability to become tanned by exposure to ultraviolet radiation according to the invention, FIG. 5 is a perspective and diagrammatical view of a skin colour reference scale for determining an individual's ability to stand exposure to ultraviolet radiation prior to erythema or for determining an individual's ability to become tanned by exposure to ultraviolet radiation according to the invention, FIG. 6 is an overall perspective view of a test bench implementation of an apparatus according to the invention for dosimetrical determination or measurement of ultraviolet radiation, said apparatus comprising a test cell to be placed on a person or an individual who is exposed to said ultraviolet radiation, and a measuring apparatus which is adapted to cooperate with the test cell and which is connected thereto through a cable and a plug, FIGS. 7a, 7b and 7c schematical views of three implementations of the test cell shown in FIG. 6 for measuring UVA, UVB, and UVC, respectively, FIG. 8 a diagrammatical view of the electronic circuitry of the measuring apparatus shown in FIG. 6, FIG. 9 a schematical and perspective view of a combined dosimeter according to the invention and a warning unit, FIG. 10 a block diagrammatical view of a combination of a dosimeter according to the invention, an apparatus according to the invention for determining an individual's ability to stand exposure to ultraviolet radiation or for determining an individual's ability to become tanned by exposure to ultraviolet radiation and/or for controlling the ultraviolet radiation to which an individual is exposed, and a warning unit, FIGS. 11a and 11b perspective views of UVB and UVC crystal dosimeters according to the invention, FIGS. 12a and 12b diagrammatical views illustrating spectral response curves of the UVB and UVC dosimeters shown in FIGS. 11a and 11b, respectively, FIG. 13a diagrammatical view illustrating the spectral response curve of the detector device included in the UVA and UVB test cells shown in FIGS. 7a and 7b, FIG. 13b a diagrammatical view illustrating the spectral response curve of the detector device included in the UVC test cell shown in FIG. 7c, FIGS. 14a, 14b and 14c diagrammatical views illustrating the total spectral response curves of the UVA, UVB and UVC dosimeter including the UVA, UVB and UVC test cells shown in FIGS. 7a, 7b, and 7c, respectively, FIGS. 15a, 15b and 15c diagrammatical views illustrating the relation between the intensity of the ultraviolet radiation to which the test cell is exposed, and the read-out of the measuring apparatus when connected to the test cells shown in FIGS. 7A, 7B and 7C, respectively, i.e. when measuring UVA, UVB and UVC, respectively, FIG. 16 a diagrammatical view illustrating the spectral response curve of the crystal of the UVB and UVC crystal dosimeters shown in FIGS. 11a and 11b, respectively, FIG. 17 a diagrammatical and sectional view of an apparatus according to the invention for dosimetrically measuring an UV-radiation dosis in which a custom designed integrated circuit chip further including a light detector is provided, FIG. 18 a block diagrammatical view of the presently preferred implementation of the electronic circuitry of the presently preferred embodiment of the apparatus shown in FIG. 3, and FIG. 19 a block diagrammatical view of the presently preferred implementation of the electronic circuitry of a modified embodiment of the apparatus shown in FIG. 3.

In FIG. 1, a diagram illustrating the results of a test comprising 26 test persons is shown. Each of the test persons or individuals had their coefficient of skin surface reflection to electromagnetic radiation of a wavelength within 503–512 nm, i.e. to visible light, registered in accordance with the principle of the present invention. Consequently, a skin surface part of each of the test persons or individuals was exposed to visible light of said predetermined spectral composition and of a predetermined intensity, and the intensity of the visible light reflected from the skin surface part of each of the individuals was measured, from which the coefficients of skin surface reflection to visible light were calculated. Thereafter, each of the individuals was exposed to artificial sun light for a period of time sufficient to just about produce erythema (the so-called MED, Minimum Erythema Dose) or for a period of time corresponding to the maximum permissible time of exposure to an ultraviolet source of said predetermined spectral composition and of said predetermined intensity. The period of time of each of the individuals was registered, and in FIG. 1 the logarithmic representation of the coefficients of reflection of each of the individuals are illustrated as a function of the period of time of exposure to said ultraviolet source of said predetermined spectral composition and said predetermined intensity of each of the individuals. As is evident from FIG. 1, there is a fairly linear correspondence between the period of time of exposure and the logarithmic representation of the coefficient of reflection of each of the 26 individuals. From this experiment it is concluded that the coefficient of skin surface reflection to visible light, e.g. light of a wavelength of 503–512 nm, may be converted into a measure representing the individual's ability to stand exposure to ultraviolet radiation prior to erythema, and that a logarithmic representation of the coefficient of skin surface reflection of each of the individuals has linear correspondence with the maximum permissible time of exposure to an ultraviolet radiation source of said predetermined intensity and of said predetermined spectral composition. It is further believed that any ultraviolet radiation of any spectral composition, i.e. composed of any UVC, UVB and UVA spectral components and of any spectral intensity distribution, may be converted into "normalised" ultraviolet radiating intensity diagrams, from which the maximum permissible time of exposure to the source in question may be determined for any individual whose coefficient of skin surface reflection has been determined in accordance with the method of the present invention.

In FIG. 2, a diagram is shown illustrating the correspondence between the coefficient of skin surface reflection and the wavelength of the electromagnetic radiation, to which the skin surface has been exposed. A full line curve designated A illustrates the response of an average non-sun tanned and non-erythrodermic skin surface part of an individual, a dot-and-dash line curve designated B illustrates the response of an erythrodermic or sun-burned skin surface part of an individual, and a dotted line curve designated C illustrates the response of a non-erythrodermic and extremely pigmented skin surface part of an individual.

In accordance with the realisation of the present invention, an individual having a high coefficient of skin surface reflection cannot stand exposure to ultraviolet radiation prior to erythema for as long a period of time as an individual having a low coefficient of skin surface reflection, provided the latter is not erythrodermic. An erythrodermic individual cannot stand exposure to ultraviolet radiation to any substantial extent. A sun tanned individual and an erythrodermic individual may be differentiated from their response curves since the response curve B, as indicated by a reference D, has a high coefficient of skin surface reflection at a wavelength of approximately 500–520 nm such as 503–512 nm, and a low coefficient of skin surface reflection at a wavelength of approximately 570–580 nm such as 574–578 nm. Therefore, provided an individual's coefficient of skin surface reflection is significantly higher at the first mentioned wavelength interval than at the last mentioned wavelength interval, the individual is erythrodermic, as is evident from FIG. 2. A non-sun tanned and non-erythrodermic individual, whose response curve is shown in FIG. 2 by the solid line curve designated A, has coefficients of skin surface reflection at the above wavelength intervals which only vary within the range of coefficient of skin surface reflection of 0.32–0.35. Therefore, provided the coefficients of skin surface reflection at the above wavelength intervals differ more than approximately 10% from one another, the individual is erythrodermic and the individual should not be exposed to ultraviolet radiation.

FIGS. 3 and 4 show a presently preferred embodiment of an apparatus according to the invention in an overall perspective view and in block-diagrammatical representation, respectively. In FIG. 3, an apparatus housing 10 is shown. The apparatus housing 10 is connected to a handset apparatus 12 through a cable 14, and the handset apparatus 12 is in an idle or non-operational mode of the apparatus received in a recess 13 of the apparatus housing 10. The apparatus housing 10 defines a front surface, in which a display 16 is arranged. In the upper part of the display 16, two digits of the alphanumeric type are provided. Below the two digits an indicator lamp 18 is arranged adjacent to an "%"-symbol, and below the indicator lamp 18, a further indicator lamp 20 is arranged adjacent to an indication "TIME MIN". On the front surface of the apparatus housing 10, four keys designated 22, 24, 26, 28 are further provided, and adjacent to the keys 24, 26, 28 three lamps designated 25, 27, and 29, respectively, are arranged.

In the idle or non-operational mode of the apparatus, the indicator lamps 18 and 20, the lamps 25, 27, 29 and the two digits display in the upper part of the display 16 are extinguished. If any of the keys 22-28 are activated or if the handset apparatus 12 is lifted off, the apparatus shifts from its idle or non-operational mode to its operational mode. In case the apparatus has been turned into its operational mode, the handset apparatus 12, which is shown in greater details in the lower part of FIG. 4, is placed on a skin surface part of an individual, whose ability to stand exposure to ultraviolet radiation is to be determined. By means of the components of the handset apparatus 12, the apparatus of the present invention determines the individual's coefficient of skin surface reflection to visible light, and converts the coefficient of skin surface reflection to a measure (% or TIME MIN) representing the individual's ability to stand exposure to ultraviolet radiation. The indication mode, i.e. either the "%"-symbol or the "TIME MIN" is selected by means of the key 22. Consequently, the two digits of the display 16 display the percentage ability of the individual to stand exposure to ultraviolet radiation or the maximum duration of exposure as expressed in minutes to the ultraviolet radiation, respectively. By means of the keys 24–28, the apparatus is informed about the type of ultraviolet ray tube or bulb assemblies, to the radiation of which the individual is to be exposed, i.e. the apparatus is informed about the intensity of the ultraviolet radiation to which the individual is to be exposed.

FIG. 4 shows a diagram of the electronic circuitry of the apparatus according to the invention. Centrally, the apparatus comprises a microprocessor, which is powered by a power supply block 32, which is constituted by a mains supply power block or preferably a battery power supply block. The microprocessor 30 and the power supplied block 32 are addressed from the keys 22, 24, 26 and 28 as described above, and the microprocessor 30 further addresses the above indicator lamps 18, 20, the lamps 25, 27, 29 and the two digits of the display 16. The handset apparatus 12 includes, as is evident from FIG. 4, a switch 38, which also addresses the microprocessor 30 and switches the apparatus from its idle or non-operational mode to its operational mode by addressing the power supply block 32. The handset apparatus 12 further includes a lamp 40, in front of which a lense or filter or a combined lense and filter 42 is arranged. The lamp 40 is activated from the microprocessor 30 provided the apparatus is in its operational mode and radiates light, preferably visible light, to an aperture of the handset apparatus 12 through the lense 42. The light radiated from the lamp 40 is directed by the lense 42 to a skin surface part of the above mentioned individual, and a part of the light transmitted to the skin surface part is reflected therefrom and transmitted or directed to a light detector 44 through a lense or filter or a combined lense and filter 46. The output of the detector 44 is connected to an input of a measuring amplifier 34, the output of which is connected to the microprocessor 30, and which preferably includes a logarithmic amplifier stage. Dependent on the activation of the keys 22–28, the coefficient of skin surface reflection of the individual is converted into a measure which is displayed by the two digits of the display 16, and which represents the individual's ability to stand exposure to ultraviolet radiation. The microprocessor 30 includes a schedule of conversion, not shown in FIG. 4, in accordance with which the measuring signal obtained from the skin surface reflection by means of the detector 44 and the measuring amplifier 34 is converted into the above measure in accordance with the principles described above with reference to FIG. 1. Furthermore, the microprocessor 30 periodically, e.g. every day, carries out a self calibration routine by employing a 100% reflection surface, not shown in FIG. 3, which is arranged in the recess 13 adjacent to the handset apparatus 12. In the apparatus shown in FIGS. 3 and 4 the lenses or filters 42 and 46 have been implemented by filters of the type Kodak Gelatine Wratten 45 and Wratten 12 and optionally combined with a colour glass filter of the type BG 18, by filters of the type Kodak Gelatine filters Wratten 45 and a colour glass filter of the type BG 18, or simply by filters of the above Kodak Gelatine filters Wratten 45 or equivalent, preferably arranged in front of the detector, or no filter at all. The detector 44 has been implemented by a photo diode (a Silicium photo diode, a GaAsP photo diode or a GaP photo diode) or a photo conductor (a CdS photo conductor).

In front of the lenses or filters 42 and 46, a covering glass plate, not shown on the drawing, is preferably arranged. The covering glass plate serves the purpose of defining a continuous and, consequently, easily cleanable out of sight surface, which further makes it easier to arrange the handset 12 in contact with the skin surface of the individual and consequently makes it easier to obtain reproduceable measuring results.

It is believed that the concept of the present invention may be implemented in numerous ways. Thus, the apparatus shown in FIG. 3 may be modified into a portable apparatus, which may further be provided with light detector means for detecting the intensity of ultraviolet radiation from a source radiating ultraviolet radiation such as the sun, a welding apparatus, an ultraviolet ray tube, etc. The measurement of the intensity of the radiation from the source is preferably, in accordance with the principles of the present invention, divided into measurements of the intensities of each of the UVC, UVB and UVA bands. The conversion of the coefficient of skin surface reflection into a measure, which is presented to an individual or an operator, is preferably carried out taking into consideration the intensities of the ultraviolet radiation of the individual UVC, UVB and UVA bands and further taking into consideration the erythema, cancer, pigmentation and any other action spectra.

It is to be emphasized that although the invention has been described with reference to individual's ability to stand exposure to ultraviolet radiation prior to erythema, the teaching of the present invention is also believed to be applicable in connection with the determination of individual's ability to stand exposure to ultraviolet radiation prior to causing other skin reactions, such as skin cancer, and further in connection with the determination of an individual's ability to become tanned by exposure to ultraviolet radiation.

As mentioned above, in accordance with the teachings of the present invention an individual's ability to stand exposure to ultraviolet radiation or an individual's ability to become tanned by exposure to ultraviolet radiation may also be determined by simply comparing at least part of the individual's skin surface to a skin colour reference scale so as to determine the individual's skin colour reference on said skin colour reference scale. In FIG. 5, a card 50 implementing a skin colour reference scale according to the invention is shown. On the upper side surface of the card 50, a skin colour reference scale 52 is arranged on the left-hand side of a central line 54 of the card. The skin colour reference scale is, as is evident from FIG. 5, divided into separate sections or fields. On the right-hand side of the central line 54 of the card 50, markings or indications 56 are arranged with reference to each section of the skin colour reference scale 52. Each of the markings or indications 56 indicate the ability of an individual with a skin tanning corresponding to a section of the skin colour reference scale referring to a marking or indication to stand exposure to ultraviolet radiation or to become tanned by exposure to ultraviolet radiation. The markings or indications may be expressed as an integer, which is to be input into a combined dosimeter and warning device according to the invention which will be described below with reference to FIG. 9, or simply as a period of time during which the individual may expose his or her body to ultraviolet radiation from a specific ultraviolet radiation source of a predetermined intensity, e.g. the radiation from an ultraviolet ray tube or ultraviolet ray bulb, to which the skin colour reference scale and/or the markings or indications 56 of the card 50 are adjusted. Alternatively, the markings or indications 56 of the card 50 may simply express the maximum permissible time period during for an individual to expose his or her body to ultraviolet radiation from the sun at a specific geographical location where the average and/or maximum ultraviolet radiation intensity from the sun has been determined as expressed in UVB and UVA and weighted, as discussed above, taking into consideration the different skin effects of the ranges and further the above action spectra.

In FIG. 6, a measuring apparatus according to the invention for dosimetrically determining or measuring the ultraviolet radiation, UVA, UVB, or UVC, to which an individual has been exposed is shown. The apparatus or dosimeter comprises a test cell 60, which will be described in greater detail below with reference to FIG. 7, and which comprises a test cell housing 62 having an outwardly protruding part 64, at the end of which a diffusor 66, preferably a diffusor having a cosine response, is arranged. The test cell 60 comprises a fixation clip 68 and a plug 70. The test cell 60 is adapted to be worn by or to be placed on an individual, who is exposed to ultraviolet radiation, e.g. in a factory, in a laboratory, or outdoor exposed to ultraviolet radiation from the sun. The test cell 60 accumulates an electrical charge corresponding to the ultraviolet radiation energy to which the individual has been exposed. After the exposure to the ultraviolet radiation, e.g. after a working day or after a predetermined period of time, the test cell 60 is connected to a measuring apparatus 80, the electronic circuitry of which is shown in FIG. 8, through a cable 72 and a plug 74 mating with the plug 70 of the test cell 60. The apparatus 80 comprises an apparatus housing 82 with a front surface 84, on which buttons 76 and 78 and provided together with a display 86. The cable 72 is also led through the front surface 84 of the apparatus housing 82.

The apparatus 80 serves the purpose of discharging the test cell 60, which, as mentioned above, contains an electric charge corresponding to the total ultraviolet radiation energy of the spectral range of UVA, UVB or UVC, in question, to which the test cell and the individual carrying the test cell have been exposed. Provided the test cell is discharged by an electric current of constant intensity, the discharging time is a measure of the electric charge and consequently a measure of the ultraviolet dose or energy to which the test cell and the individual have been exposed. The discharging time or the measure representing the ultraviolet energy, to which the discharge time is converted, is displayed on the display 86 of the apparatus 80.

Although the apparatus shown in FIG. 6 and comprising the test cell 60 and the measuring apparatus 80 may be combined into a dosimeter, it is, from a scientific and from a factory inspection point of view constructed as an apparatus comprising two parts, one of which is the test cell 60 to be carried by the individual, e.g. a worker or a member of a scientific staff, and which accumulates the dosis of ultraviolet radiation of the spectral range in question without disclosing to the individual the dosis of radiation to which the individual has been exposed. This dosis is read out by means of the measuring apparatus 80.

Basically, the test cell 60 comprises a photo detector, which generates electric current in response to exposure to electromagnetic radiation, preferably ultraviolet radiation of the spectral range in question, i.e. UVA, UVB or UVC, and which charges an accumulating unit constituted by a cell in which metal ions are transferred from a first electrode to a second electrode. The metal ions may e.g. be $Hg^{++}$ or $Ag^+$ ions. In the presently preferred embodiment of the dosimeter according to the invention, the accumulating unit is constituted by an E-cell coulometer of the type 120 FSE manufactured by Curtis Instruments Inc., and supplied from the Danish company Scansupply. Since known photo detectors do not provide selectivity to ultraviolet radiation of the spectral ranges of UVA, UVB and UVC, a filtering assembly is preferably arranged in the light path from the diffusor 66 to the photo detector of the test cell.

Figure 7A:
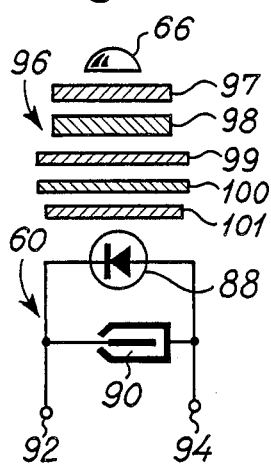
Figure 7B:
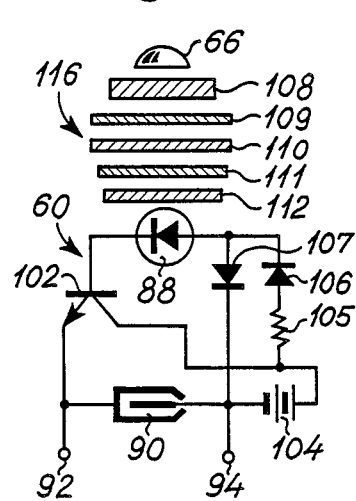
Figure 7C:
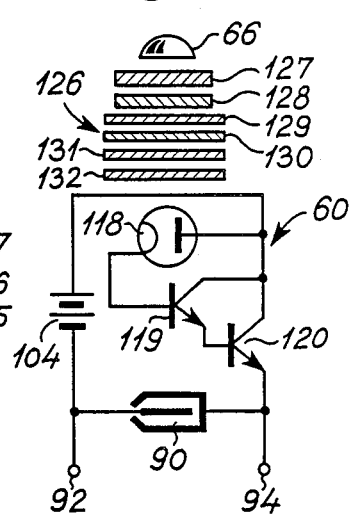

Now turning to FIG. 7, in which FIGS. 7a, 7b and 7c illustrate the presently preferred embodiments of an UVA, an UVB and an UVC embodiment of the test cell 60 respectively. The UVA test cell includes a photo detector constituted by a GaP-detector designated the reference numeral 88, which is connected to the above accumulating unit, which is designated the reference numeral 90. The GaP-detector 88, and the accumulating unit 90 are further connected to two terminals 92 and 94 constituting terminals of the plug 70 shown in FIG. 6. Between the diffusor 66 and the GaP-detector 88 a filtering assembly is arranged, which is housed in the outwardly protruding part 64 of the test cell 60 shown in FIG. 6 and designated the reference numeral 96. In the presently preferred embodiment of the UVA test cell, the filtering assembly 96 comprises four filtering components designated the reference numerals 98, 99, 100 and 101, respectively, and constituted by an 8 mm filter of the type WBS 400, a 1 mm interference filter of the type LWP 320, a 1 mm interference filter of the type SWP 400, an interference filter SWP 420. Between the filter component 98 of the filter assembly 96 and the diffusor 66, a component designated the reference numeral 97 is arranged constituted by an optical glass component of the type B270 and of a thickness of 1 mm.

Figure 13A:
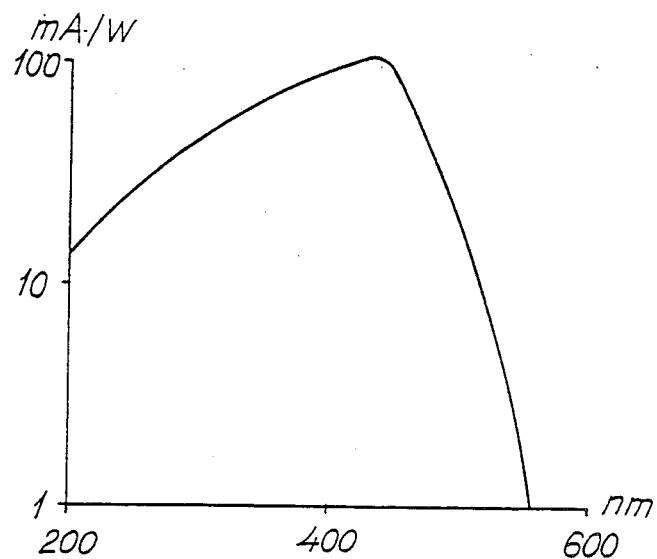
Figure 13B:
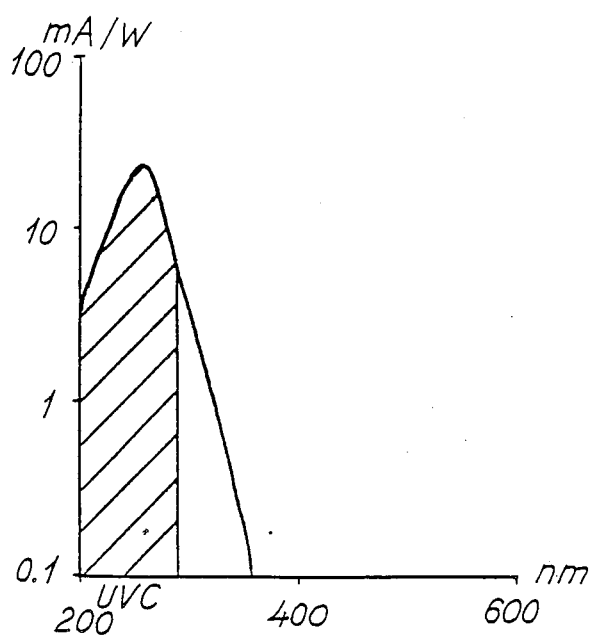
Figure 14A:
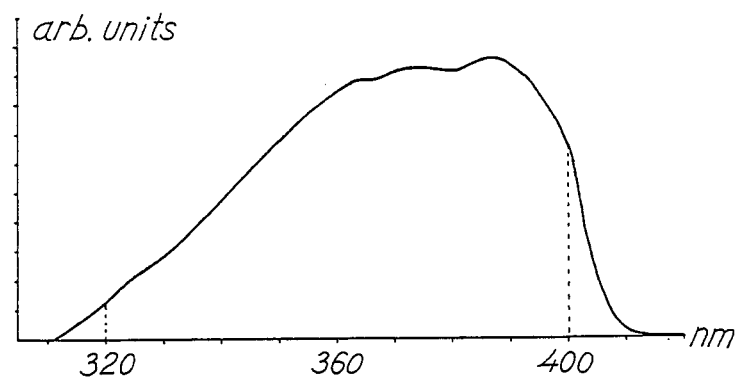
Figure 15A:
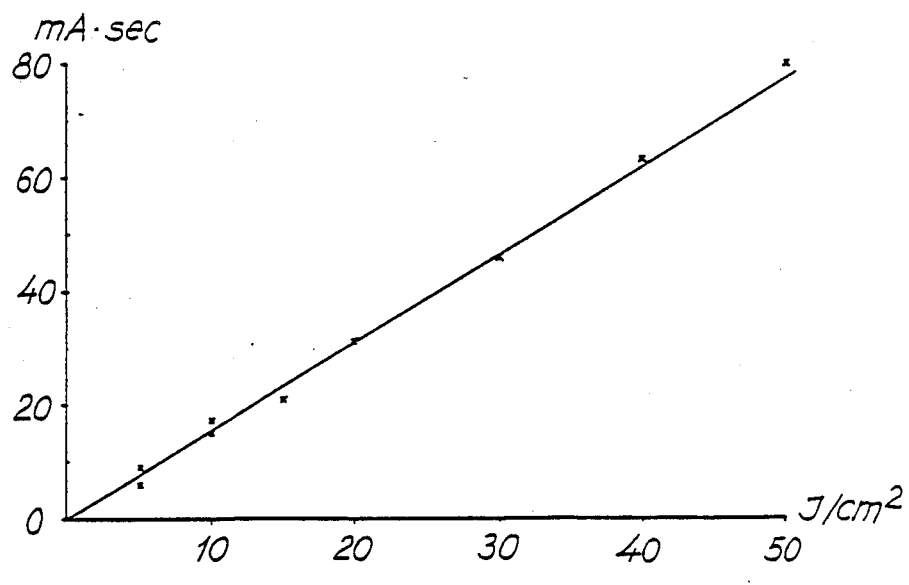

In FIG. 13a, the spectral response curve of the GaP-detector 88 manufactured by the company Hamamatsu is shown, and in FIG. 14a, the curve representing the spectral sensitivity of the UVA test cell shown in FIG. 7a when cooperating with the presently preferred embodiment of the measuring apparatus 80 is shown. In FIG. 15a, the correspondence between the dosis of ultraviolet radiation of the spectral range of UVA and the read out on the display 86 of the apparatus 80 is shown. A fairly linear relation between the dosis of UVA radiation, to which the test cell has been exposed, and the read-out from the measuring apparatus 80 is observed. In FIG. 7b, the presently preferred embodiment of an UVB test cell is shown. Like the UVA test cell shown in FIG. 7a, the UVB test cell shown in FIG. 7b includes the GaP-detector 88 and the above E-cell coulometer 90. However, since the GaP-detector 88, as is evident from FIG. 13, has a lower sensitivity to ultraviolet radiation of the spectral range of UVB than ultraviolet radiation of the spectral range of UVA, the test cell further includes an amplifier constituted by an NPN transistor 102 of the type BC 107, which is supplied from a battery supply 104 constituted by two 1.5V batteries. The test cell further includes a resistor and diode network constituted by a resistor 105 and two diodes 106 and 107. Like in FIG. 7a, the accumulating unit or the E-cell coulometer 90 is connected to the terminals 92 and 94. Between the diffusor 66 and the GaP-detector 88 a filtering assembly designated the reference numeral 116 is arranged comprising a total of five filtering components, which are designated the reference numerals 108, 109, 110, 111, and 112, respectively. The filtering component 108, which is arranged adjacent to the diffusor 66, is in the presently preferred embodiment of the UVB test cell according to the invention constituted by a 6 mm filter of the type WBS 320, the filtering component 109 is constituted by a 1 mm interference filter of the type SWP 315, the filtering component 110 is constituted by a 1 mm interference filter of the type SWP 370, the filtering component 111 is constituted by a 1 mm interference filter of the type LWP 250, and the filtering component 112 is constituted by a 1 mm interference filter of the type LWP 280.

Figure 14B:
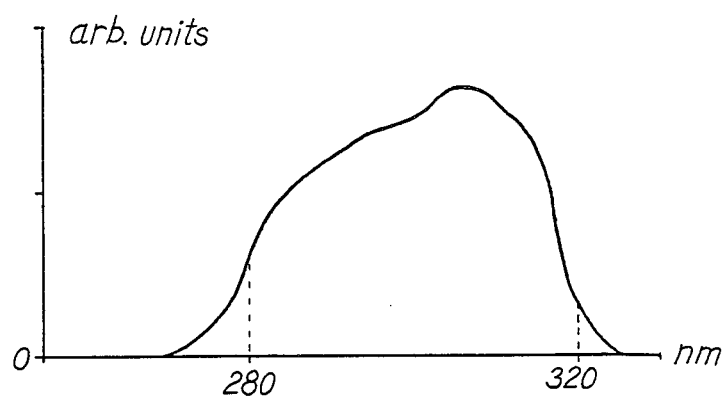

In FIG. 14b, the spectral sensitivity of the dosimeter comprising the test cell shown in FIG. 7b and including the above components and the measuring apparatus 80 is shown.

Figure 15B:
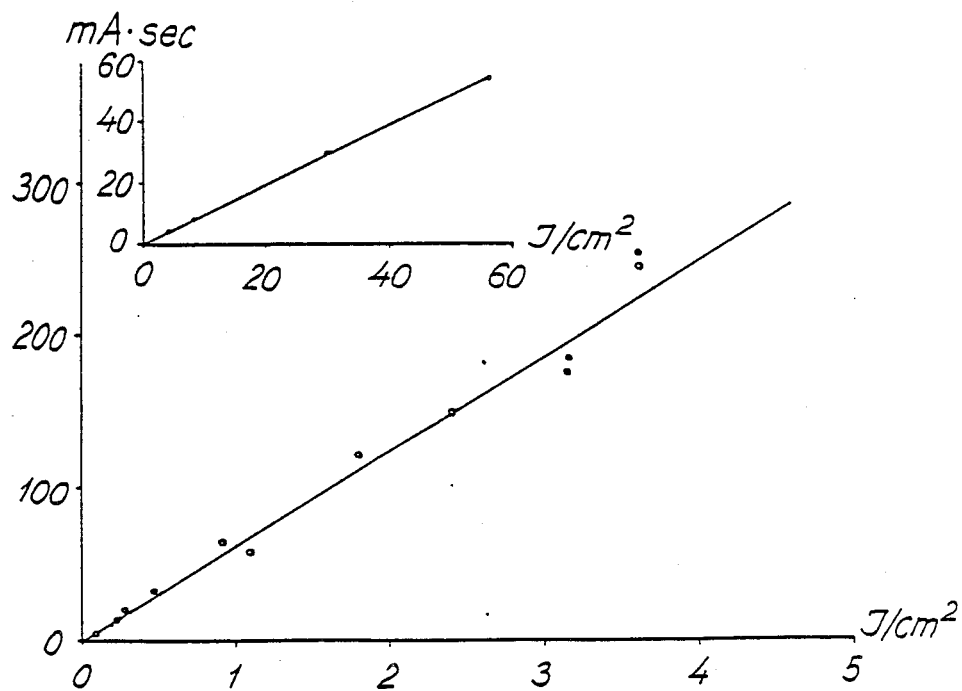
Figure 15C:
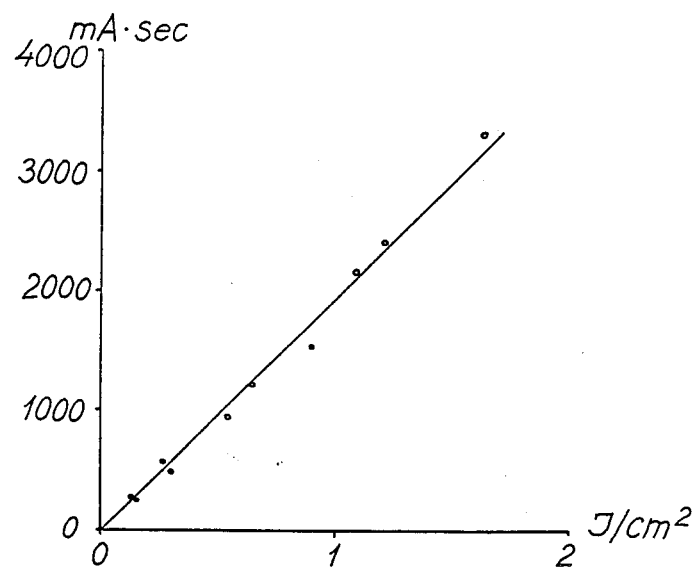

In FIG. 15b, two diagrams are shown, viz. a small diagram and a large diagram. The diagrams illustrate the correspondence between the dosis of radiation of the spectral range of UVB and the read-out on the display 86 of the measuring apparatus 80. The small diagram illustrates the correspondence without the amplifier of the UVB test cell, i.e. without the transistor 102, the battery supply 104, the resistor 105 and the diodes 106 and 107, whereas the large diagram illustrates the correspondence with the above amplifier. Linear relations of the diagrams are observed.

In FIG. 7c, the presently preferred embodiment of a UVC test cell 60 is shown. Unlike the UVA and UVB test cells described above with reference to FIGS. 7a and 7b, the UVC test cell shown in FIG. 7c comprises a photo detector of the vacuum diode type designated the reference numeral 118. The vacuum diode is in the presently preferred embodiment of the UVC test cell a vacuum diode of the type Hamamatsu R 1816. The vacuum diode 118 is biassed from the battery power supply 104, which is also shown in FIG. 7b. The signal supplied from the vacuum diode 118 is amplified in a transistor configuration of the Darlington type constituted by two NPN transistors designated 119 and 120. The NPN transistors 119 and 120 are in the presently preferred embodiment of the UVC test cell of the type BC 107. The UVC test cell also includes the above accumulating unit constituted by the above described E-cell coulometer designated the reference numeral 90 and connected to the terminals 92, 94.

Between the diffusor 66 and the photo detector constituted by the vacuum diode 118, a filtering assembly designated the reference numeral 126 is arranged. The filtering assembly 126 comprises a total of six filtering components 127, 128, 129, 130, 131, and 132. The filtering components 127 and 128 are in the presently preferred embodiment of the UVC test cell constituted by 1 mm interference filters of the type SWP 280, the filtering components 129 and 130 are constituted by 1 mm interference filters of the type SWP 310, and the filtering components 131 and 132 are constituted by 1 mm interference filters of the type SWP 350.

Figure 14C:
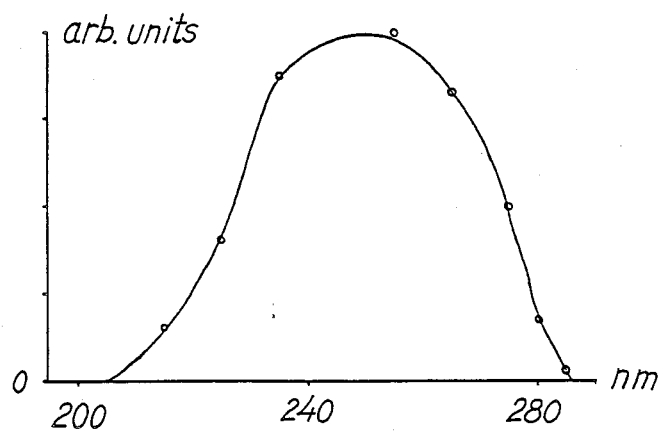

In FIG. 13b, the spectral response curve of the vacuum diode 118 of the type Hamamatsu R 1816 is shown, and in FIG. 14c the overall spectral sensitivity of the UVC dosimeter including the test cell shown in FIG. 7c when cooperating with the measuring apparatus 80 is shown. In FIG. 15c, the correspondence between the dosis of UVC radiation to which the test cell has been exposed and the read out on the display 86 of the apparatus 80 is shown. A fairly linear relation is observed.

Although the above described embodiments of the test cell 60 comprise a diffusor designated the reference numeral 66, it has been realized that the diffusor 66 may be omitted, provided the light sensitive area or the light detecting window of the detector, such as the detectors 88 and 118 shown in FIGS. 7a and 7b and in FIG. 7c, respectively, is smaller than the light transmission area of the filtering assembly, such as the filtering assembly 96, 116, and 126, shown in FIGS. 7a, 7b and 7c, respectively. In the above described embodiments, the requirement that the light detecting window of the detector is smaller than the light transmission area of the filtering assembly has been fulfilled by employing a light detector having a circular detector area of a diametre of approximately 6 mm, and a filtering assembly of a height of approximately 8 mm and having a circular light transmission area of a diametre of approximately 15 mm, in that a substantially cosine response is obtained.

Figure 8:
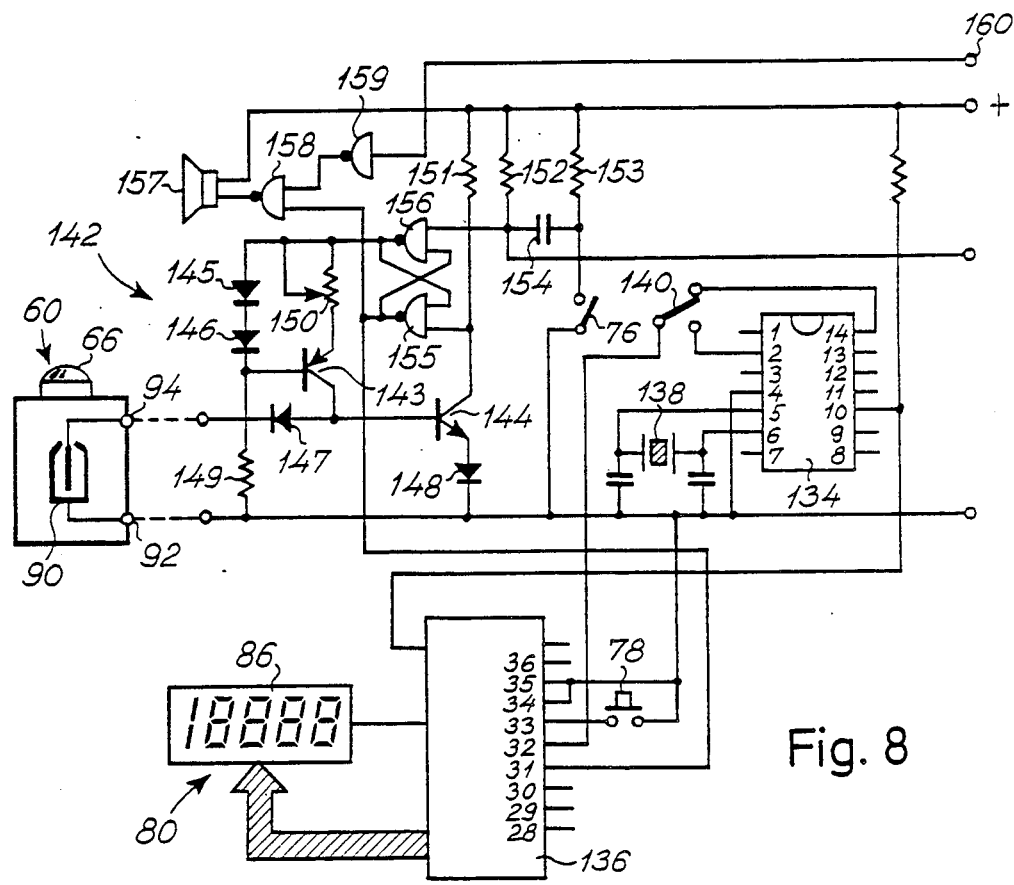

In FIG. 8, the electronic circuitry of the apparatus 80 is shown. As described above, the electronic circuitry basically serves the purpose of discharging the cell or the accumulating unit constituted by the E-cell coulometer 90 of the test cell 60 by supplying current of predetermined intensity to the test cell and by measuring the period of time during which the charging current is supplied from the measuring apparatus to the test cell. As is evident from the curves of FIGS. 15a, 15b and 15c linear relations between the electric charging current times, the discharging time periods and the doses of ultraviolet radiation or a spectral range, i.e. UVA, UVB or UVC, are obtained in accordance with the principles of the present invention. In the specification of the E-cell coulometer of the type 120 FSE, a maximum permissible discharging current of 1 mA is stated. In the presently preferred embodiment of the apparatus 80 a discharging current of 1 mA is supplied to the test cell in order to minimize the discharging time period. The electronic circuitry basically comprises a timer circuit including a first integrated circuit 134 and a second integrated circuit 136 of the type ICM 7213 and ICM 7224A manufactured by the company Intersil. The circuit configuration shown in FIG. 8 is basically identical to the circuit configuration disclosed in the Intersil application notes of the ICM 7224A and ICM 7213 circuits. Reference is made to these application notes. The first integrated circuit 134 is at its oscillator input connected to an oscillator crystal 138, which is a crystal oscillating at a frequency of 4.194304 MHz. The second integrated circuit 136 has its display drive outputs connected to the display 86. The read out on the display 86 may be reset by activating the push button 78, also shown in FIG. 6. The discharging of the E-cell coulometer 90 of the test cell 60 is started by activating the button 76, also shown in FIG. 6. By means of a switch 140, the timer circuit may be switched from an hour/-minute operational mode into an minute/second operational mode.

The electronic circuitry shown in FIG. 8 also includes a discharging current supply circuit designated the reference numeral 142 in its entity. The discharging current supply circuit 142 includes two transistors 143 and 144 constituted by transistors of the type BC 177 and BC 107, respectively. The circuit 142 also includes four diodes 145, 146, 147 and 148 preferably implemented by diodes of the type 1N 4007, resistors 149, 150, 151, 152 and 153, a capacitor 154, and two NAND gates 155 and 156 together constituting a set-reset configuration. The apparatus 80 further includes a loudspeaker 157, which is driven by two NAND gates 158 and 159. The NAND gates 158 and 159 switch a signal which is input to the apparatus through a terminal 160 to the loudspeaker 157 while the discharging current is supplied from the apparatus 80 to the test cell 60.

Figure 9:
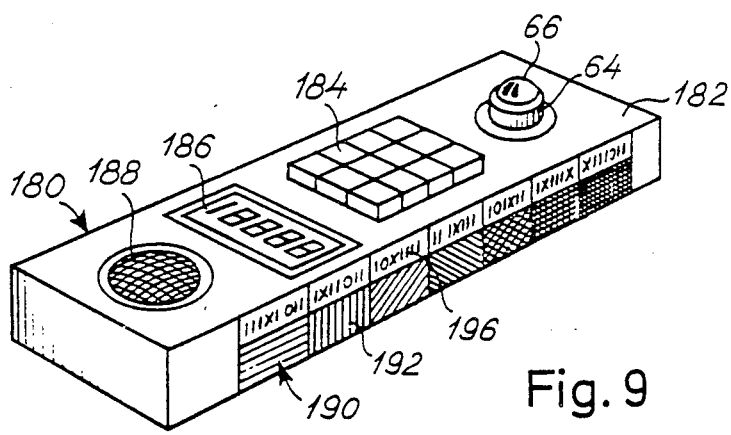
Figure 10:
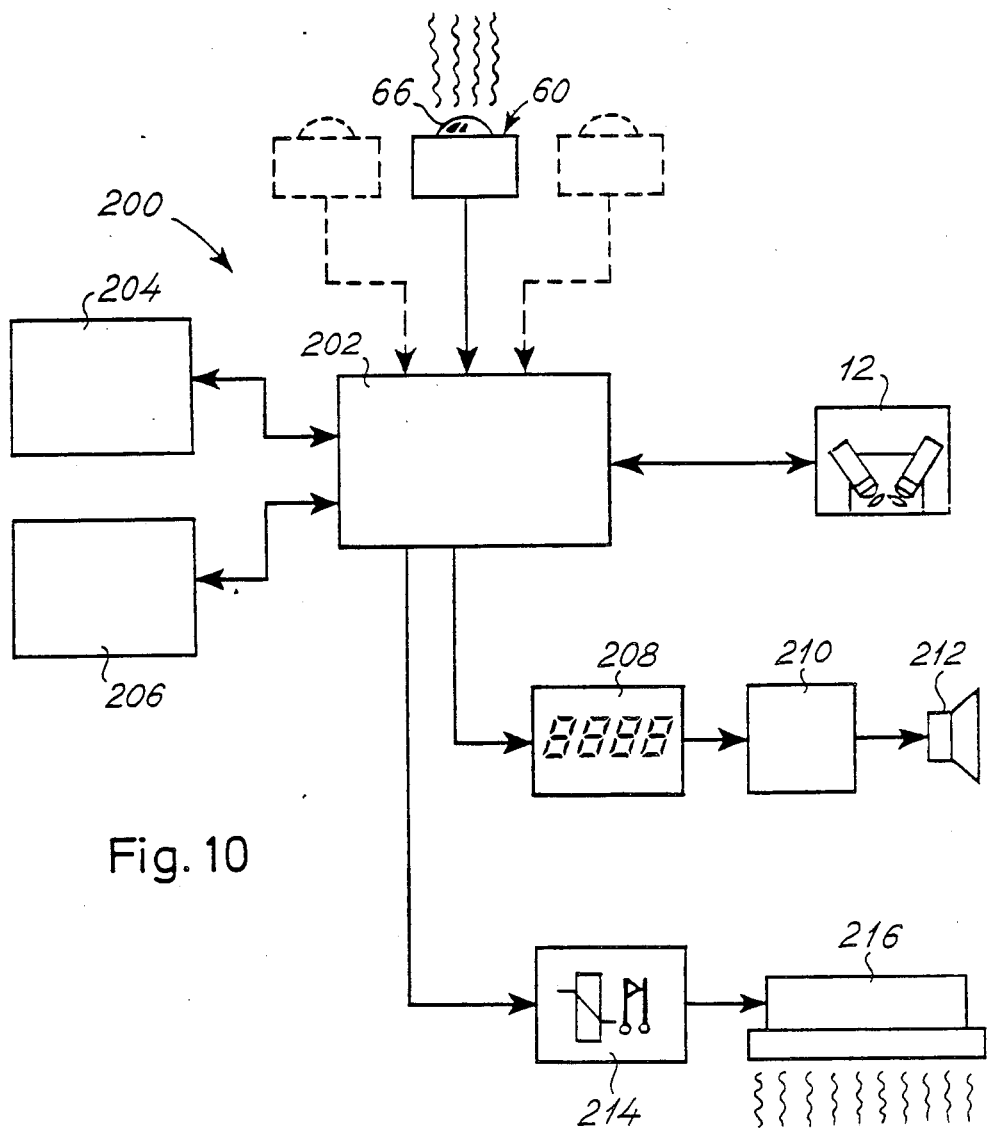

Although the above described apparatus for dosimetrical measurement or determination of ultraviolet radiation may be employed as a separate measuring apparatus, the above described dosimeter according to the invention may, in accordance with yet another aspect of the present invention, be combined with a warning unit and a skin colour reference scale according to the invention into an apparatus which is shown in FIG. 9, and which is to be described below, or be combined with a warning unit and an apparatus according to the invention for determining an individual's ability to stand exposure to ultraviolet radiation into an apparatus, which is shown in FIG. 10, and which is also to be described below.

In FIG. 9, an apparatus of the above concept, i.e. a combination of a skin colour reference scale, a dosimeter and a warning unit is shown schematically and designated the reference numeral 180 in its entity. The apparatus 180 comprises an apparatus housing 182, which defines a top surface, on which the protruding part 64 of the above described test cell 60 and the above described diffusor 66, preferably of cosine response, are mounted. On the top surface defined by the apparatus housing 182, a keyboard 184, a display 186 and a loudspeaker grille 188 is further arranged. On one of the side surfaces of the apparatus housing 182, a skin colour reference scale designated 190 basically of the concept described above with reference to FIG. 5 is arranged including skin colour reference sections 192 and corresponding markings or indications 196. The apparatus 180 shown in FIG. 9 is an apparatus intended for use by a person, who exposes his or her skin surface to an ultraviolet radiation source generating ultraviolet radiation of unknown intensity or of varying intensity, such as ultraviolet radiation from the sun.

First, the person or individual determines his or her skin colour reference on one of the sections 192 of the skin colour reference scale 190 and reads the corresponding marking or indication 196, which is a measure representing the individual's ability to stand exposure to ultraviolet radiation prior to erythema. Second, the individual inputs the marking or indication, which is preferably an integer, into a central computer means of the apparatus, not shown in FIG. 1, by means of the keyboard 184, which is preferably a numeric keyboard. The indication or integer input by means of the keyboard 184 is checked on the display 186. As will be appreciated, the central computer means of the apparatus is informed about the individual's ability to stand exposure to ultraviolet radiation or the maximum permissible dosis of ultraviolet radiation to which the individual should be exposed without becoming erythrodermic or erythematous. Third, the individual subjects the apparatus 180 to the same ultraviolet radiation as him- or herself. By means of the test cell 60 of the dosimeter part of the apparatus 180 of the which the protruding part 64 and the diffusor 66 are only shown in FIG. 9, the apparatus dosimetrially determines or measures the ultraviolet radiation energy to which the individual has been exposed. The central computer means of the apparatus 180 intermittently addresses the test cell and discharges the accumulating unit of the test cell so as to transfer the charge from the accumulating unit to the central computer means or to a storage means thereof. The central computer means of the apparatus also compares the indication input to the central computer means and representing the maximum permissible dosis of ultraviolet radiation to the value stored in the storage means of the central computer. Provided the dosis determined by means of the dosimeter of the apparatus and further stored in the storage means of the central computer means of the apparatus exceeds the maximum permissible dosis to which the individual should be exposed, the central computer means addresses the warning unit of the apparatus, which turns on a loudspeaker arranged below the loudspeaker grille 188 and generating an audible indication to the individual warning the individual that he or she should not continue the exposure to ultraviolet radiation.

Obviously, the apparatus 180 may be modified in numerous ways, thus, the display 186 may in accordance with well-known arithmetric averaging principles be employed for visually informing the individual about the estimated remaining permissible time during which the individual may expose his or her skin surface to ultraviolet radiation of an intensity determined on the basis of the intensities determined previously during the dosimetrial measuring routine. Furthermore, the light detector and the electronic circuitry of the apparatus may be integrated into a single integrated circuit chip as will be described below.

In FIG. 10, an alternative combination of an apparatus according to the invention for dosimetrical determination or measurement of ultraviolet radiation and an apparatus according to the invention for determining an individual's ability to stand exposure to ultraviolet radiation prior to causing erythema or for determining an individual's ability to become tanned and/or for controlling an individual's exposure to ultraviolet radiation is shown.

In FIG. 10, the apparatus is designated the reference numeral 200 and comprises centrally a computer 202, which is programmed for determining an individual's ability to stand exposure to ultraviolet radiation on the basis of a skin surface reflection measurement which is carried out by means of the above described handset apparatus 12, which generates a signal representing an individual's coefficient of skin surface reflection. The central computer 202 receives the measuring signal from the handset apparatus 12 and further communicates with a block 204 in which the logarithmic relationship between individuals' coefficients of skin surface reflection and individuals' ability to stand exposure to ultraviolet radiation of any intensity and of any spectral composition is stored. The central computer 202 further communicates with a block 206, in which the coefficients of skin surface reflections of different individuals, such as an erythrodermic or erythematous individual, a non-erythrodermic or non-erythematous individual and a highly pigmented individual, are stored. On the basis of the data stored in the block 206, the central computer 202 is, as described above with reference to FIG. 2, able to determine whether the individual whose skin surface reflection has been determined by means of the handset apparatus 12 is erythrodermic or non-erythrodermic and consequently whether it is recommended that the individual has his or her body exposed to ultraviolet radiation. The result of the determination of an individual's coefficient of skin surface reflection is displayed on a display 208 and further presented to the individual through an audio-amplifier 210 and a loudspeaker 212 so as to inform the individual, provided the central computer 202 has determined that the individual is erythrodermic or erythematous, that the individual should not expose his or her body to ultraviolet radiation. The central computer 202 further supplies a signal to a relay or blocking block 214, from which ultraviolet light sources or artificial ultraviolet ray tubes or bulbs 216 are powered. Provided the central computer 202 has determined that the individual is erythrodermic or erythematous, the block 214 is addressed from the central computer 202 so as to cut off the supply of power to the tubes or bulbs 216.

The apparatus 200 shown in FIG. 10 further comprises a test cell 60 which is only shown schematically and which may comprise a UVA, a UVB and/or a UVC test cell such as one or more of the test cells described above with reference to FIG. 7a, 7b, and 7c, which dosimetrically determines or measures the energy of ultraviolet radiation from the artificial ray tubes or bulbs 216 by intermittently transferring a charge from the accumulating unit or units of the test cell or test cells, respectively, to the central computer 202, in which a storage section accumulates the ultraviolet radiation energies of the individual spectral ranges of UVA, UVB and UVC so as to provide a real-time measurement of the ultraviolet radiation to which the individual has been exposed. Provided the accumulated energy values of the storage section of the central computer 202 exceeds the permissible doses to which the individual should be exposed, as determined from the individual's coefficient of skin surface reflection, the central computer 202 addresses the block 208 for visually informing the individual or an operator that the individual should not continue to expose his or her body to ultraviolet radiation from the ultraviolet ray tubes or bulbs 216 and further addresses the audio-amplifier 210 for audibly informing the individual or the operator. The central computer 202 also addresses the block 214 so as to cut off the supply of power to the ultraviolet ray tubes or bulbs 216 in case the individual or the operator has not turned off the tubes or bulbs after a predetermined short period of time after the information.

Further, the apparatus shown in FIG. 10 may be adapted to control the ultraviolet radiation to which the individual is exposed in accordance with the individual's ability to become tanned. Thus, it has been realised that individuals who are easily tanned may be tanned by exposure to ultraviolet radiation of the wavelength range of 320–400 nm (UVA) or part thereof, exclusively, while individuals who are not easily tanned, such as individuals of light skin colour, do not become tanned when exposed to ultraviolet radiation of the wavelength length range of 320–400 nm (UVA) or part thereof, exclusively. These individuals further have to be exposed to ultraviolet radiation of the wavelength range of 280–320 nm (UVB) or part thereof. In accordance with this realisation, the ultraviolet ray tubes or bulbs 216 include UVA and UVB radiating tubes, and the central computer 202 of the apparatus is further adapted to determine on the basis of the measuring signal received from the handset apparatus 12 and representing the individual's coefficient of skin surface reflection whether the individual is easily tanned or not. Provided the individual has been identified as an individual who is easily tanned, only the UVA radiating tubes or bulbs are energized. In case the individual has been identified as an individual who is not easily tanned, such as a light skin individual, only the UVB radiating tubes or bulbs which radiate only a small fraction, such as 1-2 percent of the total intensity radiated from the ultraviolet ray tubes or bulbs 216, are energized for a short period of time when the ultraviolet ray tubes or bulbs 216 are initially energized. After this short period of time, the central computer 202 turns off the UVB radiating tubes or bulbs so that only the UVA radiating tubes or bulbs are still energized. Thereupon, the apparatus continues in the above described operational mode. Instead of separate UVA and UVB radiating bulbs or tubes, the apparatus may include filtering means, which are arranged in front of the tubes or bulbs 216 and controlled by the central computer so as to control the UV-radiation from the tubes or bulbs in the above described manner.

Figure 11A:
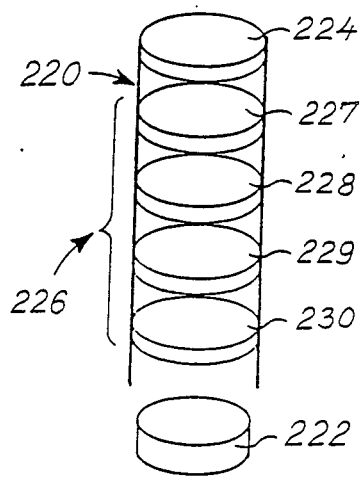
Figure 12A:
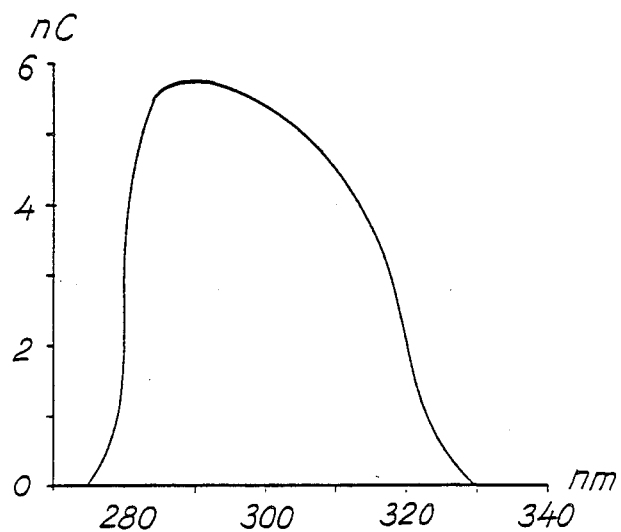
Figure 12B:
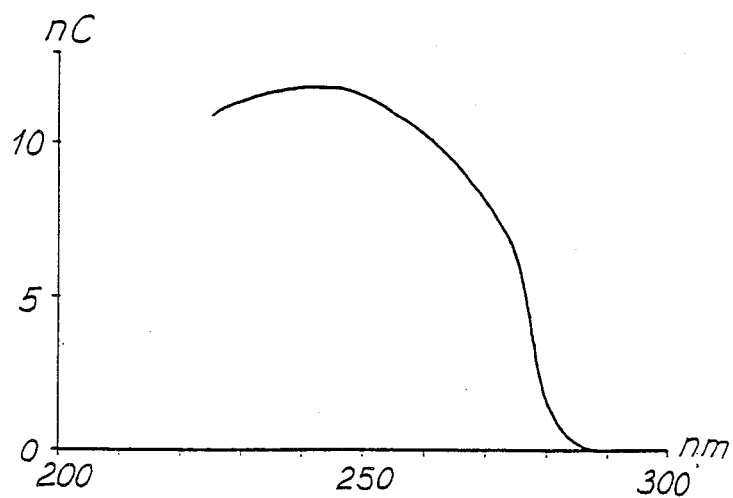

In FIG. 11a an implementation of a UVB dosimeter including a thermoluminescense crystal is shown, such as a crystal of $CaF_2:Dy$ or $CaF_2(Mn)$ which has been preheated to a high temperature such as a temperature of 800°–1000° C., e.g. 900° C. The crystals are preferably heated in an atmosphere in which the surface of the crystal is oxidized and/or heated when arranged on a ferrous material such as an iron supporting plate or on ferrous crystals such as $Fe_2O_3$ or $Fe_3O_4$ crystals. After the crystal has been exposed to ultraviolet radiation, the crystal is exposed to heat and the intensity of the light radiated from the crystal is measured. In a test setup, the thermo-luminescent crystal was arranged in a thermoluminescense detector 2000A including an automatic integrating pico ammeter, model 2000B from the company Harshaw. In the apparatus the crystal is heated in a $CO_2$ atmosphere to a temperature of 300° C. for a period of time of 90 s. By heating the crystal, the "charge" of the crystal generated by its exposure to ultraviolet radiation is radiated from the crystal.

Figure 16:
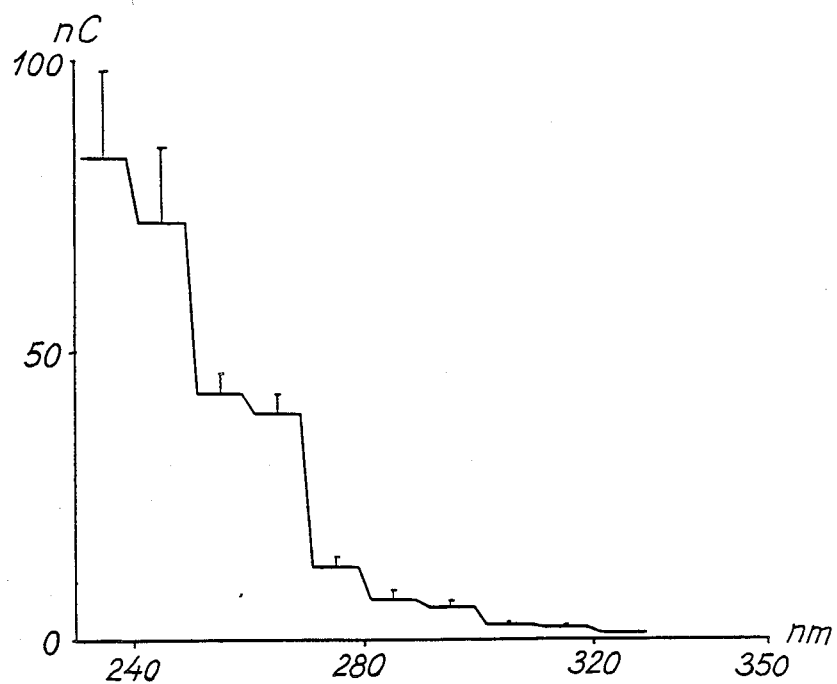

In FIG. 16, the spectral sensitivity of a total of 10 $CaF_2(Mn)$ crystals which had been exposed to ultraviolet radiation of an intensity of 10 $mJ/cm^2$ in wavelength areas and of a width of 8 mm is shown. As is evident from FIG. 16, UVB and UVC dosimeters may be implemented from a $CaF_2(Mn)$ crystal, whereas a $CaF_2(Mn)$ crystal cannot be employed for a UVA dosimeter.

In order to increase the selectivity of the UVB and UVC dosimeters, a filtering assembly is arranged between a diffusor of the dosimeter and the crystal. In FIG. 11a an exploded view of the presently preferred embodiment of an UVB dosimeter based on a $CaF_2(Mn)$ crystal is shown. The UVB dosimeter is designated the reference numeral 220 in its entity and comprises a $CaF_2(Mn)$ crystal 222, a diffusor 224, which in an alternative embodiment is a diffusor having a cosine response. Between the diffusor 224 and the crystal 220, a filtering assembly 226 is arranged comprising a total of four filtering components designated 227, 228, 229 and 230. In the presently preferred embodiment of the UVB dosimeter 220, shown in FIG. 11a, the filtering component 227 is a WG 295 filter, the filtering component 228 is a LWP 280 filter, the filtering component 229 is a SWP 370 filter, and the filtering component 230 is a SWP 320 filter. In FIG. 12A, the spectral sensitivity of the UVB dosimeter 220 is shown.

Figure 11B:
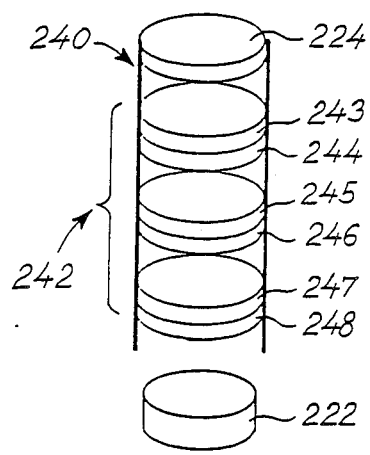

In FIG. 11b, a UVC dosimeter designated 240 in its entity is shown. The UVC dosimeter 240 is basically of a construction identical to the UVB dosimeter 220 shown in FIG. 11a. Thus, the UVC dosimeter 240 shown in FIG. 11b comprises the diffusor 224 and the CaF$_2$(Mn) crystal 222. Between the diffusor 224 and the CaF$_2$ (Mn) crystal 222 a filtering assembly 242 is arranged comprising six filtering components 243, 244, 245, 246, 247 and 248. The filtering components 243 and 244 are in the presently preferred embodiment of the dosimeter SWP 350 filters, the filtering components 245 and 246 are SWP 310 filters, and the filtering components 247 and 248 are SWP 380 filters. In FIG. 12b, the spectral sensitivity of the UVC dosimeter 240 is shown.

As mentioned above, the light detector and the electronic circuitry of the apparatus for dosimetrically measuring a UV-radiation dosis may, in accordance with the teaching of the present invention, further be integrated into a single integrated circuit chip. In FIG. 17, a further embodiment of an apparatus according to the invention or a dosimeter according to the invention including an integrated circuit chip of the above concept is shown. The dosimeter is designated the reference numeral 250 in its entity and comprises an apparatus housing 252. The apparatus housing 252 is, as will be evident from FIG. 17, of a basically pencil-like configuration. On an outer side surface of the apparatus housing 252, a diffusor 260 preferably of a cosine response, is arranged. The diffusor 260 receives electromagnetic radiation and directs the ultraviolet radiation to a mirror 262, which is preferably a semi-transparent mirror of a high reflection coefficient to ultraviolet radiation or a spectral range of ultraviolet radiation and low reflection coefficient to visible light or electromagnetic radiation outside the spectral range of ultraviolet radiation. The ultraviolet radiation received by the diffusor 260 and reflected by the mirror 262 is directed through a filtering assembly 264, which is preferably of a construction which permits that the filtering assembly may be interchanged with another filtering assembly of a different filtering response characteristic. Alternatively or additionally, the semi-transparent mirror 262 is integrated into the filtering assembly 264 and is consequently also interchangeable. In this alternative or additional embodiment, in which the semi-transparent mirror 262 is also interchangeable with an alternative mirror, the mirror is preferably transparent to a spectral range of the ultraviolet radiation exclusively and further adapted to the filter components 265 and 266 of the filtering assembly 264 in question so that the semi-transparent mirror 262 also contributes to the overall spectral filtering characteristics of the filtering assembly. The filtering assembly 264 shown in FIG. 17 includes two filter components designated 265 and 266. The filtering assembly is arranged in the light path from the mirror 262 and further from the diffusor 260 to a light detector which may be integrated into an electronic circuit chip designated 270. It is to be realised that the filtering assembly 264 and the light detector of the chip 270 are adapted to one another so that a specific overall response characteristic of the ultraviolet measuring system is obtained. In the presently preferred embodiment of the apparatus according to the invention, the light detector which is integrated into the electronic circuit chip 270 is a GaP-detector. The electronic circuit chip 270 is, as will be understod, a custom designed chip including an electronic storage means replacing the accumulating unit of the embodiment described above with reference to FIGS. 6, 7a, 7b, 7c, 8, 9 and 10. The electronic circuit of the electronic circuit chip 270 is powered from a battery 274. In accordance with the principles described above, the electronic circuit chip 270 is connected to a display 272 for displaying the dosis which has been measured cumulatively by the apparatus. The apparatus shown in FIG. 17 further includes a switch 268, which may switch the apparatus from the operational mode in which the dosis is measured cumulatively into an operational mode in which a real-time intensity measuring result is displayed on the display 272. The apparatus 250 may be held in the hands or placed on a support, e.g. on a table or the like or alternatively be mounted in a pocket of an individual who carries the dosimeter or apparatus 250. Consequently, in this pocket arrangement, the ultraviolet radiation, which is exposed to the individual is measured by the apparatus and in the above first operational mode measured cumulatively and displayed on the display 272 or in the above alternative or second operational mode measured in real-time and displayed as a real-time intensity on the display 272.

In FIG. 18, a block diagramme of the presently preferred implementation of the apparatus shown in FIGS. 3 and 4 is shown. In FIG. 18, the above described microprocessor 30, the above described display 16, the above described keys 22, 24, 26, and 28 and the above described measuring amplifier 34 constituted by a timer circuit are shown. Terminals designated 40' and 44' for providing electrical connection to the above described lamp 40 and the above described detector 44, respectively, are shown. The microprocessor 30 is, as is evident from FIG. 18, further connected to an oscillator circuit 305, constituted by a crystal oscillator and two capacitors and further connected to two microprocessors decoding blocks 301 and 302. Between the display 16 and the microprocessor 30, a display driver block 303 is arranged. The electronic circuit shown in FIG. 18 further comprises a turn-on circuit 306 including a timer circuit 304 and a turn-on button 307, which circuit 306 serves the purpose of resetting the microprocessor when the apparatus is turned on. The terminals of the components shown in FIG. 18, which terminals are not connected to a specific component or to the ground of the electronic circuitry, are connected to the positive supply voltage of the apparatus.

In the above described presently preferred implementation, the microprocessor 30 was constituted by a microprocessor circuit of the type 80C39, the timer circuits 34 and 304 were constituted by timer circuits of the type TLC555, the blocks 301 and 302 were constituted by electronic circuits of the type 27C32 and HC373, respectively, the display driver block 303 was constituted by a display driver block of the type 7211AM, and the display 16 was constituted by a four-digit LCD of the type F551153H. The crystal of the oscillator circuit 305 was a 6 MHz X-tal, and the capacitors of the oscillator circuit 305 were 22pF capacitors. The NAND gates of the turn-on circuit 306 were constituted by CMOS NAND gates of the type 4093. The detector 44, not shown in FIG. 18, was preferably of the type VT77B, in front of which a filter or a combination of filters described above with reference to FIG. 4, was arranged.

In FIG. 19, a block diagramme of the presently preferred implementation of the above described modified, portable embodiment of the apparatus of FIG. 3 is shown. The implementation shown in FIG. 19 comprises centrally a microprocessor 330, which is controlled by a crystal oscillator 305. The microprocessor 330 controls a lamp 340, which corresponds to the lamp 40 of the above described embodiment shown in FIGS.

3, 4 and 18, through a PNP transistor, which has its emitter connected to the positive supply terminal of the voltage supply terminals, which are designated the reference numeral 332'. The microprocessor 330 further receives measuring results from two light detectors, one of which is designated the reference numeral 344 and corresponds to the above described detector 44 shown in FIGS. 4 and 18, another one of which is designated the reference numeral 338, which serves the purpose of detecting the intensity of ultraviolet radiation from an external source, such as the sun, a welding apparatus, an ultraviolet ray tube or any other ultraviolet radiating source. The light detectors 344 and 338 are connected to timer circuits 334 and 336, respectively, which are further connected to the microprocessor 330 and to the positive supply terminal of the terminal 332' through a further PNP transistor, the emitter of which is connected to the above mentioned positive supply terminal. The electronic circuitry further comprises switches 322, 324, 326 and 328 corresponding to the switches or keys 22, 24, 26 and 28, respectively, shown in FIGS. 3, 4 and 18, and a display 316 corresponding to the display 16 shown in FIGS. 3, 4 and 18.

In the above described presently preferred implementation shown in FIG. 19, the microprocessor 330 was constituted a microprocessor circuit of the type TMS70CR20B, the display 316 was constituted by a two-digit LCD, the timer circuits 334 and 336 were constituted by timers of the type TLC555, the detector 344 was constituted by a detector VT77B, in front of which a filter of the type or combination described above with reference to FIG. 4 was arranged, or in front of which there was no filter at all. The detector 338 was constituted by a detector of the type VT83B, in front of which a filter of the type UG1 of a thickness of 1 mm was arranged, provided the apparatus was intended for use in solaria, or in front of which a filter of the type UG11 of a thickness of 6 mm was arranged, provided the apparatus was intended for detecting ultraviolet radiation from the sun.

Although the invention has been described with reference to a number of specific embodiments of an apparatus for determining an individual's ability to stand exposure to ultraviolet radiation or for determining an individual's ability to become tanned by exposure to ultraviolet radiation and of an apparatus for dosimetrically measuring an UV-radiation dosis, the invention may be modified in a number of ways obvious to the skilled art worker. Thus, the test cells shown in FIGS. 7a, 7b and 7c may be modified by substituting the GaP-detector 88 and possibly the vacuum diode 118 by a photo detector of the conductor type, e.g. a CdS photo conductor. Furthermore, the 1 mm interference filters of the test cells may be substituted by interference filters of a different thickness, since the thickness of the interference filters is of little importance to the characteristic of the interference filter.

Although the dosimeter according to the invention has been described with reference to ultraviolet radiation, particularly of the spectral ranges of UVA, UVB and UVC, it is, however, believed that the teaching of the present invention renders it possible to provide a universally applicable luminometer. Furthermore, it is believed that the filtering assembly of the dosimeter of the present invention may be implemented by transmission and/or reflection filtering assemblies and/or by holographic filters or any combination thereof.

I claim:

1. A method of determining an individual's ability to stand exposure to ultraviolet radiation without causing a skin reaction, such as skin cancer or erythema, comprising the following steps:
   exposing at least part of said individual's skin surface to electromagnetic radiation of a predetermined spectral composition and of a predetermined intensity,
   measuring the intensity of electromagnetic radiation reflected from said part of said individual's skin surface so as to determine the coefficient of reflection of said part to said electromagnetic radiation of said predetermined spectral composition, and
   converting said coefficient of reflection into a measure representing said individual's ability to stand exposure to ultraviolet radiation without causing said skin reaction.

2. A method according to claim 1, said electromagnetic radiation comprising spectral components within the wavelength range of 200–800 nm, preferably 400–700 nm.

3. A method of determining an individual's ability to stand exposure to ultraviolet radiation without causing a skin reaction, such as skin cancer or erythema, comprising the following steps:
   exposing at least part of said individual's skin surface to electromagnetic radiation of a predetermined spectral composition and of a predetermined intensity,
   measuring the intensity of electromagnetic radiation reflected from said part of said individual's skin surface so as to determine the coefficient of reflection of said part to said electromagnetic radiation of said predetermined spectral composition, and
   converting said coefficient of reflection into a measure in logarithmic representation and representing said individual's ability to stand exposure to ultraviolet radiation without causing said skin reaction.

4. A method of determining an individual's ability to stand exposure to ultraviolet radiation without causing a skin reaction, such as skin cancer or erythema, comprising the following steps:
   exposing at least part of said individual's skin surface to electromagnetic radiation of a predetermined spectral composition and of a predetermined intensity,
   measuring the intensity of electromagnetic radiation reflected from said part of said individual's skin surface so as to determine the coefficient of reflection of said part to said electromagnetic radiation of said predetermined spectral composition, and
   converting said coefficient of reflection into a measure representing said individual's ability to stand exposure to ultraviolet radiation without causing said skin reaction and further representing a maximum time of exposure to an ultraviolet radiation source of a predetermined intensity.

5. A method of determining an individual's ability to stand exposure to ultraviolet radiation without causing a skin reaction, such as skin cancer or erythema, comprising the following steps:
   exposing at least part of said individual's skin surface to electromagnetic radiation of a predetermined spectral composition and of a predetermined intensity,
   measuring the intensity of electromagnetic radiation reflected from said part of said individual's skin surface so as to determine the coefficient of reflection of said part to said electromagnetic radiation of said predetermined spectral composition, measuring the intensities of electromagnetic radiation within the wavelength ranges of 200–280 nm (UVC), 280–320 nm (UVB) and 320–400 nm (UVA) radiated from an electromagnetic radiation source, and converting said coefficient of reflection into a measure representing said individual's ability to stand exposure to said electromagnetic radiation of said intensities weighted by an action spectrum, such as an erythema action spectrum, a cancer action spectrum, or a pigmentation action spectrum, without causing said skin reaction.

6. A method of determining an individual's ability to stand exposure to ultraviolet radiation without causing a skin reaction, such as skin cancer or erythema, comprising the following steps:

exposing at least part of said individual's skin surface to electromagnetic radiation of at least a first and a second wavelength and of a predetermined intensity, said first wavelength being a wavelength at which erythrodermic skin reflection is high, and said second wavelength being a wavelength at which erythrodermic skin reflection is low, measuring the intensity of electromagnetic radiation reflected from said part of said individual's skin surface so as to determine the coefficients of reflection of said part to said electromagnetic radiation of said first and second wavelength, converting said coefficients of reflection into a measure representing said individual's ability to stand exposure to ultraviolet radiation without causing said skin reaction, and comparing said coefficients of reflection so as to determine if said skin surface part is erythrodermic.

7. A method according to claim 6, said first wavelength being of the order of approximately 500–520 nm such as 503–512 nm, and said second wavelength being of the order of approximately 535–540 nm such as 538 nm.

8. A method according to claim 6, said first wavelength being of the order of approximately 500–520 nm such as 503–512 nm, and said second wavelength being of the order of approximately 570–580 nm such as 574–578 nm.

9. A method of determining an individual's ability to become tanned by exposure to ultraviolet radiation, comprising the following steps:

exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said part to said electromagnetic radiation of said predetermined spectral composition, and converting said coefficient of reflection into a measure representing said individual's ability to become tanned by exposure to ultraviolet radiation.

10. A method according to claim 9, said electromagnetic radiation comprising spectral components within the wavelength range of 200–800 nm, preferably 400–700 nm.

11. A method of determining an individual's ability to become tanned by exposure to ultraviolet radiation, comprising the following steps:

exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said part to said electromagnetic radiation of said predetermined spectral composition, and converting said coefficient of reflection into a measure in logarithmic representation and representing said individual's ability to become tanned by exposure to ultraviolet radiation.

12. A method of determining an individual's ability to become tanned by exposure to ultraviolet radiation, comprising the following steps:

exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said part to said electromagnetic radiation of said predetermined spectral composition, and converting said coefficient of reflection into a measure representing said individual's ability to become tanned by exposure to ultraviolet radiation and further representing a maximum time of exposure to an ultraviolet radiation source of a predetermined intensity.

13. A method of determining an individual's ability to become tanned by exposure to ultraviolet radiation, comprising the following steps:

exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said electromagnetic radiation of said predetermined spectral composition, measuring the intensities of electromagnetic radiation within the wavelength ranges of 200–280 nm (UVC), 280–320 nm (UVB) and 320–400 nm (UVA) radiated from an electromagnetic radiation source, and converting said coefficient of reflection into a measure representing said individual's ability to become tanned by exposure to said ultraviolet radiation of said intensities weighted by an action spectrum, such as an erythema action spectrum, a cancer action spectrum, or a pigmentation action spectrum.

14. A method of determining an individual's ability to become tanned by exposure to ultraviolet radiation, comprising the following steps:

exposing at least part of said individual's skin surface to electromagnetic radiation of at least a first and second wavelength and of a predetermined intensity, said first wavelength being a wavelength at which erythrodermic skin reflection is high, and said second wavelength being a wavelength at which erythrodermic skin reflection is low, measuring the intensity of electromagnetic radiation reflected from said part of said individual's skin surface so as to determine the coefficients of reflection of said part to said electromagnetic radiation of said first and second wavelength, converting said coefficient of reflection into a measure representing said individual's ability to become tanned by exposure to ultraviolet radiation, and comparing said coefficients of reflection so as to determine if said skin surface part is erythrodermic.

15. A method according to claim 14, said first wavelength being of the order of approximately 500–520 nm such as 503–512 nm, and said second wavelength being of the order of approximately 535–540 nm such as 538 nm.

16. A method according to claim 14, said first wavelength being of the order of approximately 500–520 nm such as 503–512 nm, and said second wavelength being of the order of approximately 570–580 nm such as 574–578 nm.

17. A method of controlling an individual's exposure to ultraviolet radiation, comprising the following steps:
determining if said individual's skin surface is easily tanned by exposure to ultraviolet radiation or if said individual's skin surface is not easily tanned by exposure to ultraviolet radiation, and exposing said individual's skin surface to ultraviolet radiation of the wavelength range of 320–400 nm (UVA) exclusively, provided said individual's skin surface has been determined as being easily tanned by exposure to ultraviolet radiation, or alternatively, additionally exposing for a period of time said individual's skin surface to a low intensity ultraviolet radiation of the wavelength range of 280–320 nm (UVB) or part thereof, provided said individual's skin surface has been determined as not being easily tanned by exposure to ultraviolet radiation so as to start melanogenesis by stimulation of the melanocytes.

18. A method according to claim 17, said determining step comprising:
exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said part to said electromagnetic radiation of said predetermined spectral composition, and converting said coefficient of reflection into a measure representing said individual's ability to stand exposure to ultraviolet radiation without causing said skin reaction.

19. A method according to claim 17, said determining step comprising:
exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said part to said electromagnetic radiation of said predetermined spectral composition, and converting said coefficient of reflection into a measure in logarithmic representation and representing said individual's ability to stand exposure to ultraviolet radiation without causing said skin reaction.

20. A method according to claim 17, said determining step comprising:
exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said part to said electromagnetic radiation of said predetermined spectral composition, and converting said coefficient of reflection into a measure representing said individual's ability to stand exposure to ultraviolet radiation without causing said skin reaction and further representing a maximum time of exposure to an ultraviolet radiation source of a predetermined intensity.

21. A method according to claim 17, said determining step comprising:
exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said part to said electromagnetic radiation of said predetermined spectral composition, measuring the intensities of electromagnetic radiation within the wavelength ranges of 200–280 nm (UVC), 280–320 nm (UVB) and 320–400 nm (UVA) radiated from an electromagnetic radiation source, and converting said coefficient of reflection into a measure representing said individual's ability to stand exposure to said electromagnetic radiation of said intensities weighted by an action spectrum, such as an erythema action spectrum, a cancer action spectrum, or a pigmentation action spectrum, without causing said skin reaction.

22. A method according to claim 17, said determining step comprising:
exposing at least part of said individual's skin surface to electromagnetic radiation of at least a first and a second wavelength and of a predetermined intensity, said first wavelength being a wavelength at which erythrodermic skin reflection is high, and said second wavelength being a wavelength at which erythrodermic skin reflection is low, measuring the intensity of electromagnetic radiation reflected from said part of said individual's skin surface so as to determine the coefficients of reflection of said part to said electromagnetic radiation of said first and second wavelength, converting said coefficients of reflection into a measure representing said individual's ability to stand exposure to ultraviolet radiation without causing said skin reaction, and comparing said coefficients of reflection so as to determine if said skin surface part is erythrodermic.

23. A method according to claim 17, said determining step comprising:
exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said part to said electromagnetic radiation of said predetermined spectral composition, and converting said coefficient of reflection into a measure representing said individual's ability to become tanned by exposure to ultraviolet radiation.

24. A method according to claim 17, said determining step comprising:

exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said part to said electromagnetic radiation of said predetermined spectral composition, and converting said coefficient of reflection into a measure in logarithmic representation and representing said individual's ability to become tanned by exposure to ultraviolet radiation.

25. A method according to claim 17, said determining step comprising:

exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said part to said electromagnetic radiation of said predetermined spectral composition, and converting said coefficient of reflection into a measure representing said individual's ability to become tanned by exposure to ultraviolet radiation and further representing a maximum time of exposure to an ultraviolet radiation source of a predetermined intensity.

26. A method according to claim 17, said determining step comprising:

exposing at least part of said individual's skin surface to electromagnetic radiation of a predetermined spectral composition and of a predetermined intensity, measuring the intensity of electromagnetic radiation reflected from said part of said individual's skin surface so as to determine the coefficient of reflection of said part to said electromagnetic radiation of said predetermined spectral composition, measuring the intensities of electromagnetic radiation within the wavelength ranges of 200–280 nm (UVC), 280–320 nm (UVB) and 320–400 nm (UVA) radiated from an electromagnetic radiation source, and converting said coefficient of reflection into a measure representing said individual's ability to become tanned by exposure to said ultraviolet radiation of said intensities weighted by an action spectrum, such as a erythema action spectrum, a cancer action spectrum, or a pigmentation action spectrum.

27. A method according to claim 17, said determining step comprising:

exposing at least part of said individual's skin surface to electromagnetic radiation of at least a first and a second wavelength and of a predetermined intensity, said first wavelength being a wavelength at which erythrodermic skin reflection is high, and said second wavelength being a wavelength at which erythrodermic skin reflection is low, measuring the intensity of electromagnetic radiation reflected from said part of said individual's skin surface so as to determine the coefficients of reflection of said part to said electromagnetic radiation of said first and second wavelength, converting said coefficient of reflection into a measure representing said individual's ability to become tanned by exposure to ultraviolet radiation, and comparing said coefficients of reflection so as to determine if said skin surface part is erythrodermic.

28. An apparatus for determining an individual's ability to stand exposure to ultraviolet radiation without causing a skin reaction, such as skin cancer or erythema, comprising:

an electromagnetic source for generating electromagnetic radiation, an electromagnetic detector for detecting the intensity of any electromagnetic radiation exposed to said detector and for generating an electrical signal in response to said exposure to said electromagnetic radiation, a first means for directing at least part of said electromagnetic radiation generated by said electromagnetic source to a part of said individual's skin surface so as to expose said part of said individual's skin surface to electromagnetic radiation of a predetermined spectral composition and of a predetermined intensity, a second means for directing electromagnetic radiation reflected from said part of said individual's skin surface to said electromagnetic detector, and a measuring and converting means connected to said electromagnetic detector for measuring and converting said electrical signal generated by said electromagnetic detector into a measure representing said individual's ability to stand exposure to ultraviolet radiation without causing said skin reaction.

29. An apparatus according to claim 28, said electromagnetic source generating said electromagnetic radiation comprising spectral components within the wavelength range of 200–800 nm, preferably 400–700 nm.

30. An apparatus according to claim 28, further comprising:

a central control means controlling the overall operation of the apparatus and further the conversion of said electrical signal into said measure.

31. An apparatus according to claim 30, said central control means being a microprocessor means, and said central control means including a storage means for storing a schedule representing said conversion of said electrical signal into said measure.

32. An apparatus according to claim 28, further comprising:

a display means connected to said measuring and converting means for displaying said measure.

33. An apparatus according to claim 28, comprising:

a third means for measuring the intensities of electromagnetic radiation within the wavelength range of 200–280 nm (UVC), 280–320 nm (UVB) and 320–400 nm (UVA), said third means being connected to said measuring and converting means, and said electrical signal being converted by said measuring and converting means into a measure representing said individual's ability to stand exposure to electromagnetic radiation of said intensities.

34. An apparatus for determining an individual's ability to stand exposure to ultraviolet radiation without causing a skin reaction, such as skin cancer or erythema, comprising:

an electromagnetic source for generating electromagnetic radiation, an electromagnetic detector for detecting the intensity of any electromagnetic radiation exposed to said detector and for generating an electrical signal in response to said exposure to said electromagnetic radiation, a first means for directing at least part of said electromagnetic radiation generated by said electromagnetic source to a part of said individual's skin surface so as to expose said part of said individual's skin surface to electromagnetic radiation of a predetermined spectral composition and of a predetermined intensity, a second means for directing electromagnetic radiation reflected from said part of said individual's skin surface to said electromagnetic detector, and a measuring and converting means comprising a logarithmic converting means connected to said electromagnetic detector for measuring and converting said electrical signal generated by said electromagnetic detector into a measure in logarithmic representation and representing said individual's ability to stand exposure to ultraviolet radiation without causing said skin reaction.

35. An apparatus for determining an individual's ability to stand exposure to ultraviolet radiation without causing a skin reaction, such as skin cancer or erythema, comprising:

an electromagnetic source for generating electromagnetic radiation, an electromagnetic detector for detecting the intensity of any electromagnetic radiation exposed to said detector and for generating an electrical signal in response to said exposure to said electromagnetic radiation, a first means for directing at least part of said electromagnetic radiation generated by said electromagnetic source to a part of said individual's skin surface so as to expose said part of said individual's skin surface to electromagnetic radiation of a predetermined spectral composition and of a predetermined intensity, a second means for directing electromagnetic radiation reflected from said part of said individual's skin surface to said electromagnetic detector, and a measuring and converting means connected to said electromagnetic detector for measuring and converting said electrical signal generated by said electromagnetic detector into a measure representing said individual's ability to stand exposure to ultraviolet radiation without causing said skin reaction, and further representing a maximum of time of exposure to an ultraviolet radiation source of a predetermined intensity.

36. An apparatus for determining an individual's ability to become tanned by exposure to ultraviolet radiation, comprising:

an electromagnetic source for generating electromagnetic radiation, an electromagnetic detector for detecting the intensity of any electromagnetic radiation exposed to said detector and for generating an electrical signal in response to said exposure to said electromagnetic radiation, a first means for directing at least part of said electromagnetic radiation generated by said electromagnetic source to a part of said individual's skin surface so as to expose said part of said individual's skin surface to electromagnetic radiation of a predetermined spectral composition and of a predetermined intensity, a second means for directing electromagnetic radiation reflected from said part of said individual's skin surface to said electromagnetic detector, and a measuring and converting means connected to said electromagnetic detector for measuring and converting said electrical signal generated by said electromagnetic detector into a measure representing said individual's ability to become tanned by exposure to ultraviolet radiation.

37. An apparatus according to claim 36, said electromagnetic source generating said electromagnetic radiation comprising spectral components within the wavelength range of 200-800 nm, preferably 400-700 nm.

38. An apparatus according to claim 36, further comprising:

a central control means controlling the overall operation of the apparatus and further the conversion of said electrical signal into said measure.

39. An apparatus according to claim 38, said central control means being a microprocessor means, and said central control means including a storage means for storing a schedule representing said conversion of said electrical signal into said measure.

40. An apparatus according to claim 36, further comprising:

a display means connected to said measuring and converting means for displaying said measure.

41. An apparatus according to claim 36 comprising:

a third means for measuring the intensities of electromagnetic radiation within the wavelength range of 200-280 nm (UVC), 280-320 nm (UVB) and 320-400 nm (UVA), said third means being connected to said measuring and converting means, and said electrical signal being converted by said measuring and converting means into a measure representing said individual's ability to stand exposure to electromagnetic radiation of said intensities.

42. An apparatus for determining an individual's ability to become tanned by exposure to ultraviolet radiation, comprising:

an electromagnetic source for generating electromagnetic radiation, an electromagnetic detector for detecting the intensity of any electromagnetic radiation exposed to said detector and for generating an electrical signal in response to said exposure to said electromagnetic radiation, a first means for directing at least part of said electromagnetic radiation generated by said electromagnetic source to a part of said individual's skin surface so as to expose said part of said individual's skin surface to electromagnetic radiation of a predetermined spectral composition and of a predetermined intensity, a second means for directing electromagnetic radiation reflected from said part of said individual's skin surface to said electromagnetic detector, and a measuring and converting means comprising a logarithmic converting means connected to said electromagnetic detector for measuring and converting said electrical signal generated by said electromagnetic detector into a measure in logarithmic representation and representing said individual's ability to become tanned by exposure to ultraviolet radiation.

43. An apparatus for determining an individual's ability to become tanned by exposure to ultraviolet radiation, comprising:
   an electromagnetic source for generating electromagnetic radiation,
   an electromagnetic detector for detecting the intensity of any electromagnetic radiation exposed to said detector and for generating an electrical signal in response to said exposure to said electromagnetic radiation,
   a first means for directing at least part of said electromagnetic radiation generated by said electromagnetic source to a part of said individual's skin surface so as to expose said part of said individual's skin surface to electromagnetic radiation of a predetermined spectral composition and of a predetermined intensity,
   a second means for directing electromagnetic radiation reflected from said part of said individual's skin surface to said electromagnetic detector, and
   a measuring and converting means connected to said electromagnetic detector for measuring and converting said electrical signal generated by said electromagnetic detector into measure representing said individual's ability to become tanned by exposure to ultraviolet radiation and further representing a maximum of time of exposure to an ultraviolet radiation source of a predetermined intensity.

44. An apparatus for dosimetrically measuring an UV-radiation dosis comprising:
   an ultraviolet filtering assembly including at least one filter of a specific filtering response for receiving ultraviolet radiation at an input of the ultraviolet filtering assembly and for filtering the ultraviolet radiation output from the ultraviolet filtering assembly in accordance with said specific filtering response of said at least one filter thereof,
   a light detector for receiving ultraviolet radiation from said filtering assembly and for generating an electric signal in response to said ultraviolet radiation received from said filtering assembly, and
   an accumulator means for receiving said signal from said light detector and for cumulatively registering said signal, said ultraviolet filtering assembly and said light detector together defining a specific ultraviolet response characteristic, and said specific ultraviolet response characteristic being a UVA response, a UVB response, a UVC response, an erythema action response, a cancer action response or a pigmentation action response.

45. An apparatus according to claim 44, said light detector being a GaP-detector.

46. An apparatus according to claim 44, said accumulator means being constituted by a coulometer cell.

47. An apparatus according to claim 44, said accumulator means being constituted by an electronic measuring means.

48. An apparatus according to claim 44, further comprising a diffusor for receiving and directing said ultraviolet radiation to said input of said ultraviolet filtering assembly, said diffusor having a substantially cosine response.

49. An apparatus according to claim 44, said filtering assembly being of the transmission filtering type, of the reflection filtering type, of the holographic type or of any combination thereof.

50. A method of determining an individual's skin tanness, comprising the following steps:
   exposing at least part of said individual's skin surface to electromagnetic radiation of a predetermined spectral composition and of a predetermined intensity;
   measuring the intensity of electromagnetic radiation reflected from said part of said individual's skin surface so as to determine the coefficient of reflection of said part of said electromagnetic radiation of said predetermined spectral composition; and
   converting said coefficient of reflection into a measure representing said individual's skin tanness.

51. A method according to claim 50, said electromagnetic radiation comprising spectral components within the wavelength range of 200–800 nm, preferably 400–700 nm.

52. A method of determining an individual's skin tanness comprising the following steps:
   exposing at least part of said individual's skin surface to electromagnetic radiation of a predetermined spectral composition and of a predetermined intensity;
   measuring the intensity of electromagnetic radiation reflected from said part of said individual's skin surface so as to determine the coefficient of reflection of said part to said electromagnetic radiation of said predetermined spectral composition; and
   converting said coefficient of reflection into a measure in logarithmic representation and representing said individual's skin tanness.

53. A method of determining an individual's skin tanness, comprising the following steps:
   exposing at least part of said individual's skin surface to electromagnetic radiation of a least a first and a second wavelength and of a predetermined intensity, said first wavelength being a wavelength at which erythrodermic skin reflection is high, and said second wavelength being a wavelength at which erythrodermic skin reflection is low;
   measuring the intensity of electromagnetic radiation reflected from said part of said individual's skin surface so as to determine the coefficients of reflection of said part to said electromagnetic radiation of said first and second wavelength; and
   comparing said coefficients of reflection so as to determine if said skin surface part is tanned or erythrodermic.

54. A method according to claim 53, said first wavelength being of the order of approximately 500–520 nm such as 503–512 nm, and said second wavelength being of the order of approximately 535–540 nm such as 538 nm.

55. A method according to claim 54, said first wavelength being of the order of approximately 500–520 nm such as 503–512 nm, and said second wavelength being of the order of approximately 570–580 nm such as 574–578 nm.

56. A method of determining an individual's skin pigmentation, comprising the following steps:
   exposing at least part of said individual's skin surface to electromagnetic radiation of a predetermined spectral composition and of a predetermined intensity;

measuring the intensity of electromagnetic radiation reflected from said part of said individual's skin surface so as to determine the coefficient of reflection of said part to said electromagnetic radiation of said predetermined spectral composition; and converting said coefficient of reflection into a measure representing said individual's skin pigmentation.

57. A method according to claim 56, said electromagnetic radiation comprising spectral components within the wavelength range of 200–800 nm, preferably 400–700 nm.

58. A method of determining an individual's skin pigmentation, comprising the following steps:

exposing at least part of said individual's skin surface to electromagnetic radiation of a predetermined spectral composition and of a predetermined intensity;

measuring the intensity of electromagnetic radiation reflected from said part of said individual's skin surface so as to determine the coefficient of reflection of said part of said electromagnetic radiation of said predetermined spectral composition; and converting said coefficient of reflection into a measure in logarithmic representation and representing said individual's skin pigmentation.

59. A method of determining an individual's skin pigmentation, comprising the following steps:

exposing a least part of said individual's skin surface to electromagnetic radiation of at least a first and a second wavelength and of a predetermined intensity, said first wavelength being a wavelength at which erythrodermic skin reflection is high, and said second wavelength being a wavelength at which erythrodermic skin reflection is low;

measuring the intensity of electromagnetic radiation reflected from said part of said individual's skin surface so as to determine the coefficients of reflection of said part to said electromagnetic radiation of said first and second wavelength; and comparing said coefficients of reflection so as to determine if said skin surface part is pigmentated or erythrodermic.

60. A method according to claim 59, said first wavelength being of the order of approximately 500–520 nm such as 503–512 nm, and said second wavelength being of the order of approximately 535–540 nm such as 538 nm.

61. A method according to claim 59, said first wavelength being of the order of approximately 500–520 nm such as 503–512 nm, and said second wavelength being of the order of approximately 570–580 nm such as 574–578 nm.

62. An apparatus for determining an individual's skin tanness, comprising:

an electromagnetic source for generating electromagnetic radiation;

an electromagnetic detector for detecting the intensity of any electromagnetic radiation exposed to said detector and for generating an electrical signal in response to said exposure to said electromagnetic radiation;

a first means for directing at least part of said electromagnetic radiation generated by said electromagnetic source to a part of said individual's skin surface so as to expose said part of said individual's skin surface to electromagnetic radiation of a predetermined spectral composition and of a predetermined intensity;

a second means for directing electromagnetic radiation reflected from said part of said individual's skin surface to said electromagnetic detector; and a measuring and converting means connected to said electromagnetic detector for measuring and converting said electrical signal generated by said electromagnetic detector into a measure representing said individual's skin tanness.

63. An apparatus according to claim 62, said electromagnetic source generating said electromagnetic radiation comprising spectral components within the wavelength range of 200–800 nm, preferably 400–700 nm.

64. An apparatus according to claim 62, further comprising:

a central control means controlling the overall operation of the apparatus and further the conversion of said electrical signal into said measure.

65. An apparatus according to claim 64, said central control means being a microprocessor means, and said central control means including a storage means for storing a schedule representing said conversion of said electrical signal into said measure.

66. An apparatus according to claim 62, further comprising:

a display means connected to said measuring and converting means for displaying said measure.

67. An apparatus for determining an individual's skin tanness, comprising:

an electromagnetic source for generating electromagnetic radiation;

an electromagnetic detector for detecting the intensity of any electromagnetic radiation exposed to said detector and for generating an electrical signal in response to said exposure to said electromagnetic radiation;

a first means for directing at least part of said electromagnetic radiation generated by said electromagnetic source to a part of said individual's skin surface so as to expose said part of said individual's skin surface to electromagnetic radiation of a predetermined spectral composition and of a predetermined intensity;

a second means for directing electromagnetic radiation reflected from said part of said individual's skin surface to said electromagnetic detector; and a measuring and converting means comprising a logarithmic converting means connected to said electromagnetic detector for measuring and converting said electrical signal generated by said electromagnetic detector into a measure in logarithmic representation and representing said individual's skin tanness.

68. An apparatus for determining an individual's skin pigmentation, comprising:

an electromagnetic source for generating electromagnetic radiation;

an electromagnetic detector for detecting the intensity of any electromagnetic radiation exposed to said detector and for generating an electrical signal in response to said exposure to said electromagnetic radiation;

a first means for directing at least part of said electromagnetic radiation generated by said electromagnetic source to a part of said individual's skin surface so as to expose said part of said individual's skin surface to electromagnetic radiation of a predetermined spectral composition and of a predetermined intensity;

a second means for directing electromagnetic radiation reflected from said part of said individual's skin surface to said electromagnetic detector; and a measuring and converting means connected to said electromagnetic detector for measuring and converting said electrical signal generated by said electromagnetic detector into a measure representing said individual's skin pigmentation.

69. An apparatus according to claim 68, said electromagnetic source generating said electromagnetic radiation comprising spectral components within the wavelength range of 200-280 nm, preferably 400-700 nm.

70. An apparatus according to claim 68, further comprising:

a central control means controlling the overall operation of the apparatus and further the conversion of said electrical signal into said measure.

71. An apparatus according to claim 70, said central control means being a microprocessor means, and said central control means including a storage means for storing a schedule representing said conversion of said electrical signal into said measure.

72. An apparatus according to claim 68, further comprising:

a display means connected to said measuring and converting means for displaying said measure.

73. An apparatus for determining an individual's skin pigmentation, comprising:

an electromagnetic source for generating electromagnetic radiation;

an electromagnetic detector for detecting the intensity of any electromagnetic radiation exposed to said detector and for generating an electrical signal in response to said exposure to said electromagnetic radiation a first means for directing a least part of said electromagnetic radiation generated by said electromagnetic source to a part of said individual's skin surface so as to expose said part of said individual's skin surface to electromagnetic radiation of a predetermined spectral composition and of a predetermined intensity;

a second means for directing electromagnetic radiation reflected from said part of said individual's skin surface to said electromagnetic detector; and a measuring and converting means comprising a logarithmic converting means connected to said electromagnetic detector for measuring and converting said electrical signal generated by said electromagnetic detector into a measure in logarithmic representation and representing said individual's skin pigmentation.

* * * * *